United States Patent
Hotta

(10) Patent No.: US 12,285,272 B2
(45) Date of Patent: Apr. 29, 2025

(54) MEASURING DEVICE

(71) Applicant: TDK CORPORATION, Tokyo (JP)

(72) Inventor: Yu Hotta, Tokyo (JP)

(73) Assignee: TDK CORPORATION, Tokyo (JP)

( * ) Notice: Subject to any disclaimer, the term of this patent is extended or adjusted under 35 U.S.C. 154(b) by 114 days.

(21) Appl. No.: 18/135,275

(22) Filed: Apr. 17, 2023

(65) Prior Publication Data

US 2023/0329641 A1 Oct. 19, 2023

(30) Foreign Application Priority Data

Apr. 19, 2022 (WO) ................. PCT/JP2022/018156
Feb. 1, 2023 (JP) ................................. 2023-014194

(51) Int. Cl.
*A61B 5/00* (2006.01)
*A61B 5/243* (2021.01)

(52) U.S. Cl.
CPC ............ *A61B 5/6889* (2013.01); *A61B 5/243* (2021.01); *A61B 2562/222* (2013.01)

(58) Field of Classification Search
CPC . A61B 5/6889; A61B 5/243; A61B 2562/222; A61B 5/702; A61B 5/7207
See application file for complete search history.

(56) References Cited

U.S. PATENT DOCUMENTS

| | | | |
|---|---|---|---|
| 6,332,324 B1 | 12/2001 | Saho et al. | |
| 2008/0076996 A1* | 3/2008 | Hoarau | A61B 5/7207 600/323 |
| 2009/0058661 A1* | 3/2009 | Gleckler | A47C 31/126 340/573.7 |
| 2009/0295385 A1* | 12/2009 | Brazdeikis | A61B 5/242 324/309 |
| 2020/0178827 A1 | 6/2020 | Al-Shimary et al. | |
| 2020/0237243 A1* | 7/2020 | Kawabata | G01R 33/0094 |
| 2024/0065570 A1* | 2/2024 | Sundholm | A61B 5/05 |

FOREIGN PATENT DOCUMENTS

| | | | |
|---|---|---|---|
| CN | 104730142 B | * | 11/2017 |
| JP | H08-126624 A | | 5/1996 |
| JP | H09-140683 A | | 6/1997 |
| JP | 2020-521564 A | | 7/2020 |
| WO | 99/64796 A1 | | 12/1999 |
| WO | 2019/077865 A1 | | 4/2019 |

OTHER PUBLICATIONS

CN-104730142-B Translation (Year: 2017).*
Sep. 11, 2023 Search Report issued in European Patent Application No. 23168250.1.

* cited by examiner

*Primary Examiner* — Alexei Bykhovski
(74) *Attorney, Agent, or Firm* — Oliff PLC

(57) ABSTRACT

Provided is a measuring device that can ensure a level of a measurement signal while noise derived from the body movement of a subject is curbed.

A measuring device according to the embodiments includes a first fixing body, a sensor fixing body configured to fix a sensor for detecting a biological signal, and the sensor, in which the first fixing body and the sensor fixing body have separate structures.

11 Claims, 12 Drawing Sheets

MEASURING DEVICE

CROSS-REFERENCE TO RELATED APPLICATION

Priority is claimed on Japanese Patent Application No. 2023-014194, filed Feb. 1, 2023 and International Patent Application No. PCT/JP2022/018156, filed Apr. 19, 2022, the contents of which are incorporated herein by reference.

BACKGROUND OF THE INVENTION

Field of the Invention

The present disclosure relates to a measuring device.

Description of Related Art

Measuring devices for measuring a biological signal, such as an electrocardiogram or a magnetocardiogram, caused by the activity of the human heart are known.

In such a measuring device, for example, when a subject and a sensor are in direct contact, or when the movement of a subject is indirectly, transmitted to a sensor, noise derived from the body movement such as the breathing or heartbeat of the subject may occur in the measurement signal.

In the method described in Patent Document 1, analyzing the magnetic field in the body area of a subject is performed using a magnetometer system. In the method, a filter is used to attenuate the noise derived from the body movement of a subject (refer to Patent Document 1).

PATENT DOCUMENTS

[Patent Document 1] Published Japanese Translation No. 2020-521564 of the PCT International Publication

SUMMARY OF THE INVENTION

However, in the conventional method, removal of noise derived from body movement has been insufficient in some cases.

For example, frequency filtering using a high-pass filter or low-pass filter is known as a typical noise removal method, but when a frequency band of a signal to be measured (a signal of interest) and a frequency band of noise derived from the body movement are close to each other, the removal of noise by the frequency filtering will also affect (attenuate) the signal of interest.

As a specific example, a frequency band of a T wave (approximately 4 to 7 Hz) of an electrocardiogram (or a magnetocardiogram) has been removed by filtering, in some cases.

In addition, conventionally, when measurement is performed without bringing a subject and a sensor into contact, a distance between the subject and the sensor has been too far to detect a measurement signal with sufficient strength, or it has been difficult to maintain a posture of the subject during the measurement.

The present disclosure is made in view of the circumstances described above, and provides a measuring device, which can ensure a level of a measurement signal while curbing noise derived from the body movement of a subject.

According to one aspect, a measuring device includes a first fixing body, a sensor fixing body configured to fix a sensor for detecting a biological signal, and the sensor, in which the first fixing body and the sensor fixing body have separate structures.

According to the measuring device according to the present disclosure, it is possible to ensure a level of a measurement signal while noise derived from the body movement of a subject is curbed.

DETAILED DESCRIPTION OF THE INVENTION

Figure 1:
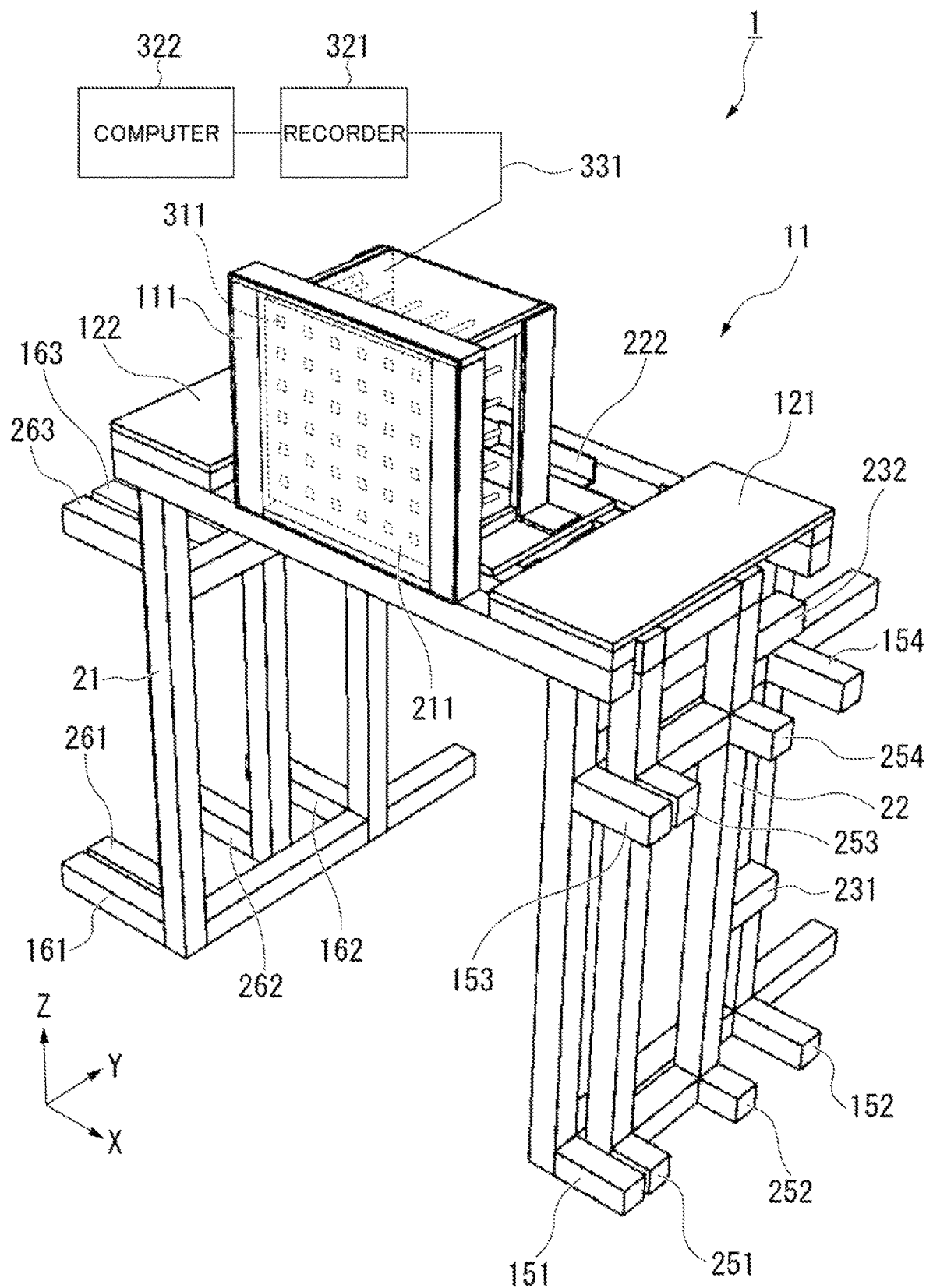
FIG. 1 is a diagram which shows a schematic configuration example of a measurement system including a measuring device according to a first embodiment.

Hereinafter, the present embodiment will be described in detail with reference to the drawing as appropriate.

In the present embodiment, a shape or a size of each member (component), or a relationship between two or more members are exemplified, but these may not necessarily be strictly configured as exemplified in the present embodiment, and for example, errors such as manufacturing errors may be included to the extent that there is no practical problem.

As a specific example, words that express the relationship of two or more members include parallel, equal (the same), and the like, but these may not necessarily be strictly configured as exemplified in the present embodiment, and for example, errors such as manufacturing errors may be included to the extent that there is no practical problem.

First Embodiment

In the present embodiment, the same configuration will be described with reference to FIGS. 1 to 8. For convenience of description, some of the components are omitted and symbols of some of the components are omitted in some illustrations.

[Measurement System]

FIG. 1 is a diagram which shows a schematic configuration example of a measurement system 1 including a measuring device 11 according to a first embodiment.

For convenience of description, FIG. 1 shows an XYZ orthogonal coordinate system, which is a three-dimensional orthogonal coordinate system. In the present embodiment, for convenience of description, a positive direction of an X-axis is a right direction, a negative direction of the X-axis is a left direction, a positive direction of a Y-axis is a backward direction, and a negative direction of the Y-axis is a forward direction, a positive direction of a Z-axis is an upward direction, and a negative direction of the Z-axis is a downward direction.

The measurement system 1 includes the measuring device 11, a recorder 321, a computer 322, and a cable 331.

The cable 331 connects a sensor 311 provided in the measuring device 11 and the recorder 321 in a communicative manner.

The sensor 311 measures (detects) a predetermined physical quantity and transmits information on a result of the measurement to the recorder 321 via the cable 331.

The recorder 321 has a memory, receives the information on a result of the measurement transmitted from the sensor 311 via the cable 331, and stores (records) the received information in the memory. The computer 322 is connected to the recorder 321 in a communicative manner, reads the information on a result of the measurement, stored in the memory of the recorder 321, and performs predetermined processing. The predetermined processing may be any processing.

Here, although one sensor 311 attached to the measuring device 11 is shown in the example of FIG. 1, a plurality of sensors may be attached to the measuring device 11. In this case, for example, each sensor is connected to the recorder 321 via a cable in a communicative manner, and the recorder 321 stores the information on a result of the measurement for these sensors.

In addition, although the wired cable 331 is shown in the example of FIG. 1, a wireless line may be used instead of the wired cable 331. In this case, wireless communication between the sensor 311 and the recorder 321 is performed.

In the present embodiment, the recorder 321, the computer 322, the cable 331, and the sensor 311 are described as external apparatuses (devices) to the measuring device 11. However, as another example, one or more of the recorder 321, the computer 322, the cable 331, and the sensor 311 may be regarded to be included in the measuring device 11.

Moreover, for example, some or all parts of the measuring device 11 may be regarded as a jig.

<Measuring Device>

Figure 2:
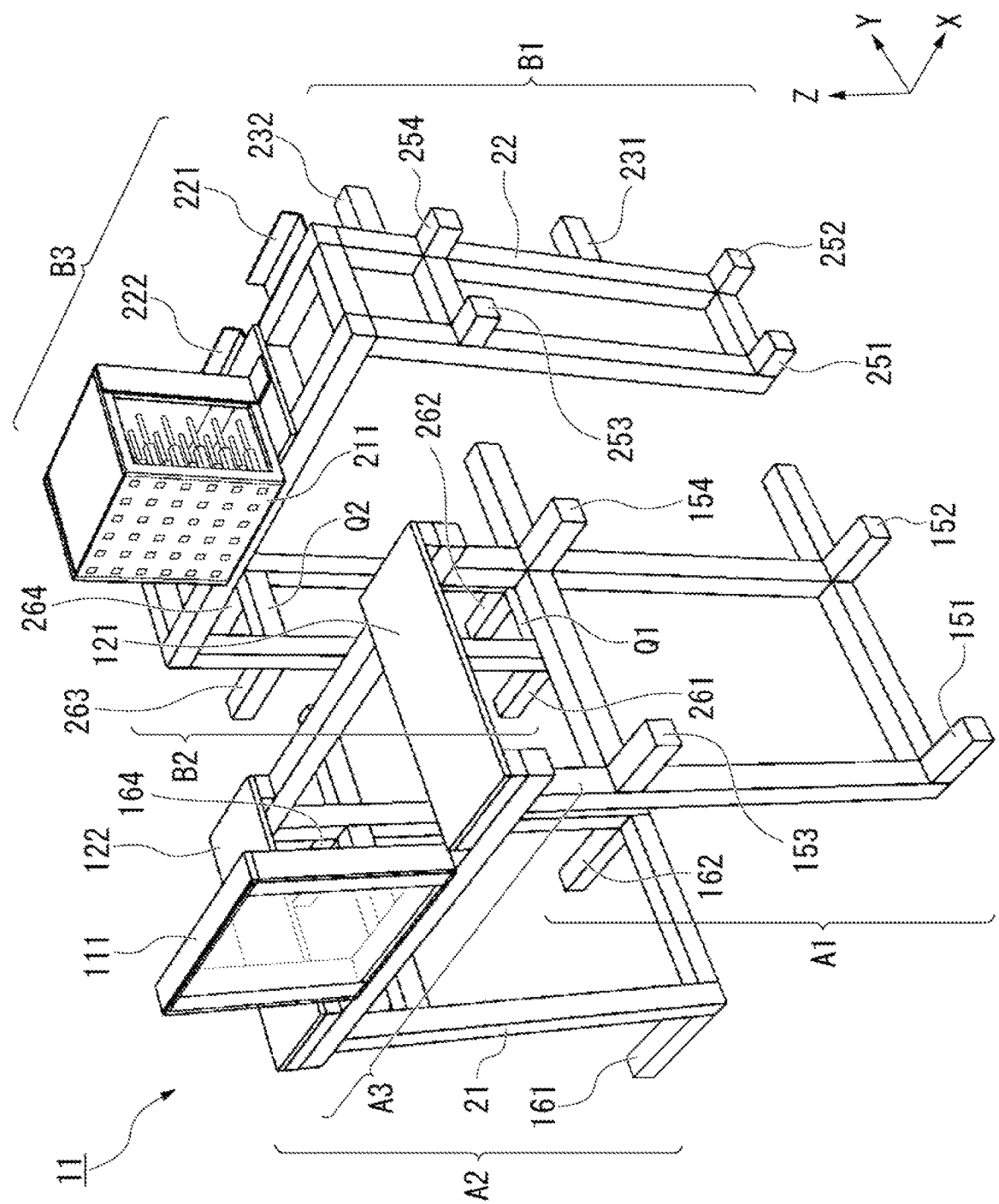
FIG. 2 is a diagram which shows a configuration example of each of a subject fixing body and a sensor fixing body constituting the measuring device according to the first embodiment.

FIG. 2 is a diagram which shows configuration examples of each of a subject fixing body 21 and a sensor fixing body 22 that constitute the measuring device 11 according to the first embodiment.

For convenience of description, FIG. 2 shows an XYZ orthogonal coordinate system similar to that of FIG. 1.

Here, FIG. 1 shows a state in which the subject fixing body 21 and the sensor fixing body 22 are combined as a state when the measuring device 11 is used.

On the other hand, in FIG. 2, the subject fixing body 21 and the sensor fixing body 22 are shown to be separated for convenience of description.

A configuration example of the subject fixing body 21 will be described.

The subject fixing body 21 includes a right leg portion A1, a left leg portion A2, and a platform portion A3.

The right leg portion A1 is configured by combining a plurality of rectangular parallelepiped members, and as a whole, is a leg-shaped member having a predetermined height (a vertical distance).

The left leg portion A2 is configured by combining a plurality of rectangular parallelepiped members, and as a whole, is a leg-shaped member having a predetermined height (a vertical distance).

Here, the height of the right leg portion A1 and the height of the left leg portion A2 are equal to each other.

Schematically, the right leg portion A1 and the left leg portion A2 have a configuration in which two rectangular parallelepiped members each extending in a vertical direction are fixed by one or more members extending in a horizontal direction (in a direction perpendicular to the vertical direction).

The right leg portion A1 has two protruding portions 151 and 152 that protrude to a right side at positions of the lower end.

In addition, the right leg portion A1 has two protruding portions 153 and 154 that protrude to a right side at positions in the middle in the vertical direction.

Protrusion lengths of these four protruding portions 151 to 154 to the right side are equal to each other.

The left leg portion A2 has two protruding portions 161 and 162 that protrude to a left side at positions of the lower end.

In addition, the left leg portion A2 has two protruding portions 163 and 164 that protrude to the left side at positions in the middle in the vertical direction.

Protrusion lengths of these four protruding portions 161 to 164 to the left side are equal to each other.

The positions of the protruding portions 151 to 154 from the right leg portion A1 and the positions of the protruding portions 161 to 164 from the left leg portion A2 may not necessarily be bilaterally symmetrical, and, for example, a configuration in which some positions are bilaterally symmetrical and other positions are not bilaterally symmetrical may also be used. In addition, the positions of the protruding portions 151 to 154 from the right leg portion A1 and the positions of the protruding portions 161 to 164 from the left leg portion A2 may be all bilaterally symmetrical.

The platform portion A3 includes a component in which a plurality of rectangular parallelepiped members disposed on an upper surface of the right leg portion A1 and an upper surface of the left leg portion A2 are combined.

Schematically, the platform portion A3 has a configuration in which two rectangular parallelepiped members extending in a lateral direction are fixed by one or more members extending in a depth direction (a direction connecting a front side and a back side).

In addition, the platform portion A3 includes a plate 111 disposed at an upper center of the component, a right hand rest 121 disposed at an upper right side of the component, and a left hand rest 122 disposed at an upper left side of the component.

Here, the plate 111 includes a frame having a rectangular (for example, square) surface and a film-shaped member provided on the surface of the frame. The film shaped member is, for example, transparent, or translucent, and is made of a material that does not affect measurement by the sensor 311.

The plate 111 is disposed so that a surface of the frame is parallel to an XZ plane and the frame is positioned on a front side of the platform portion A3. The frame extends upward from the platform portion A3.

The right hand rest 121 is a plate-shaped member and is disposed on a right side of the plate 111. A surface of the right hand rest 121 is parallel to an XY plane and has a rectangular surface. The surface has, for example, long sides extending from the front to the back and short sides extending from the left to the right.

The left hand rest 122 is a plate-shaped member and is disposed on a left side of the plate 111. A surface of the left hand rest 122 is parallel to the XY plane and has a rectangular surface. The surface has, for example, long sides extending from the front to the back, and short sides extending from the left to the right.

Here, the left hand rest 122 and the right hand rest 121 are disposed bilaterally symmetrically with respect to the plate 111.

Here, the right hand rest 121 and the left hand rest 122 may each be configured to be, for example, detachable from the platform portion A3, or may be inseparably fixed to the platform portion A3.

The right hand rest 121 and left hand rest 122 may each be attached to the platform portion A3 using, for example, a screw, a fixing band, a single-sided or double-sided adhesive tape, a hook-and-loop fasteners, an adhesive, or the like.

Moreover, in the present embodiment, the right hand rest 121 and the left hand rest 122 may have rectangular plate surfaces, but as another configuration example, they may have plate surfaces in a shape including curved portions.

In addition, for example, each surface of the right hand rest 121 and the left hand rest 122 may also be configured so that a positional relationship with respect to a top surface of the platform portion A3 (for example, a mutual angular relationship in a surface parallel to the XY plane) can be adjusted.

In addition, for example, one or both of the right hand rest 121 and the left hand rest 122 may be connected to one of a front side or a back side of the platform portion A3 by a hinge. In this case, the hand rests (one or both of the right hand rest 121 and the left hand rest 122) connected by the hinge can be opened and closed with respect to the platform portion A3 by opening and closing the hinge. As a result, for example, the hinge can be opened when an operation is performed in which the subject fixing body 21 and the sensor fixing body 22 are combined, and the hinge can be closed during measurement by the measuring device 11.

In the present embodiment, it is shown that the platform portion A3 includes two hand rests (the right hand rest 121 and the left hand rest 122), but as another configuration example, a configuration in which any one of these two hand rests is provided and the other is not provided, or a configuration in which none of these two hand rests is provided may be used.

A configuration example of the sensor fixing body 22 will be described.

The sensor fixing body 22 includes a right leg portion B1, a left leg portion B2, and a platform portion B3.

The right leg portion B1 is configured by combining a plurality of rectangular parallelepiped members, sand as a whole is a leg-shaped member having a predetermined height (a vertical distance).

The left leg portion B2 is configured by combining a plurality of rectangular parallelepiped members, and as a whole is a leg-shaped member having a predetermined height (a vertical distance).

Here, the height of the right leg portion B1 and the height of the left leg portion B2 are equal to each other.

The right leg portion B1 has two protruding portions 251 and 252 that protrude to the right side at positions of the lower end.

In addition, the right leg portion B1 has two protruding portions 253 and 254 that protrude to the right side at positions in the middle in the vertical direction.

Protrusion lengths of these four protruding portions 251 to 254 to the right are equal to each other.

The right leg portion B1 has two protruding portions 231 and 232 that protrude to a back side at positions in the middle in the vertical direction.

These two protruding portions 231 and 232 are disposed at positions with different heights.

Protrusion lengths of these two protruding portions 231 and 232 to the back side are equal to each other.

In the present embodiment detailed description of these two protruding portions 231 and 232 is omitted, but they may be used for positioning and the like.

Schematically, the right leg portion B1 and the left leg portion B2 have a configuration in which two rectangular parallelepiped members each extending in the vertical direction are fixed by one or more members extending in the horizontal direction (a direction perpendicular to the vertical direction).

The left leg portion B2 includes two protruding portions 261 and 262 that protrude to the left at positions of the lower end.

In addition, the left leg portion B2 includes two protruding portions 263 and 264 that protrude to the left at positions in the middle in the vertical direction.

Protrusion lengths of these four protruding portions 261-264 to the left are equal to each other.

The positions of the protruding portions 251 to 254 from the right leg portion B1 and the positions of the protruding portions 261 to 264 from the left leg portion B2 may be, for example, all bilaterally symmetrical. In addition, the positions of the protruding portions 251 to 254 from the right leg portion B1 and the positions of the protruding portions 261 to 264 from the left leg portion B2 may not necessarily be all bilaterally symmetrical, and, for example, configurations in which some positions are bilaterally symmetrical and other positions are not bilaterally symmetrical may also be used.

The platform portion B3 includes a component in which a plurality of rectangular parallelepiped members disposed on an upper surface of the right leg portion B1 and an upper surface of the left leg portion B2 are combined.

Schematically, the platform portion B3 has a configuration in which two rectangular parallelepiped members extending in the lateral direction are fixed by one or more members extending in the depth direction (the direction connecting the front side and the back side).

In addition, the platform portion B3 includes a sensor holding portion 211 disposed at an upper center of the component.

The sensor holding portion 211 has a rectangular parallelepiped housing, and is provided with a part for mounting a plurality of sensors (for example, a sensor similar to the sensor 311 shown in FIG. 1) inside the housing.

In the present embodiment, a surface on front side of the sensor holding portion 211 is a surface parallel to the XZ plane, and is configured so that two or more sensors can be mounted in each of the vertical direction and the horizontal direction. In other words, it is configured so, that a plurality of sensors can be disposed in a matrix shape on the surface of the front side of the sensor holding portion 211. The sensor holding portion 211 that holds the matrix-shaped sensors may be called, for example, a sensor array portion.

Here, in the present embodiment, it is shown that a surface of a frame of the plate 111 is parallel to the XZ plane and the surface of the front side of the sensor holding portion 211 is also parallel to the XZ plane, but they may not necessarily be parallel to the XZ plane.

For example, the surface of the frame of the plate 111 and the surface of the front side of the sensor holding portion 211 may be a plane non-parallel to the XZ plane (that is, a plane not parallel to the XZ plane), or may be a curved surface.

The surface of the frame of the plate 111 and the surface of the front side of the sensor holding portion 211 may be, for example, surfaces of the same shape or may be surfaces of different shapes, so that the surface of the front side of the sensor holding portion 211 may be covered with the surface of the frame of the plate 111.

In the state in which the subject fixing body 21 and the sensor fixing body 22 are combined, the surface of the front side of the sensor holding portion 211 is disposed at a position facing a surface of a back side of the plate 111. In the present embodiment, these two surfaces have substantially the same shape. The shape is, for example, a rectangular (including square) shape.

In addition, the platform portion B3 includes two cable holding portions (cable receivers) 221 and 222 that protrude from the component to the back side.

The cable holding portion 221 is disposed on a right side of the sensor holding portion 211 in the lateral direction.

The cable holding portion 222 is disposed at a position overlapping the sensor holding portion 211 in the lateral direction (for example, in a center in the lateral direction).

Note that the platform portion B3 may further include a cable holding portion disposed at a left side of the sensor holding portion 211 in the lateral direction.

Here, the cable holding portions 221 and 222 can support, for example, a cable connecting, a sensor and the recorder 321 (for example, a cable similar to the cable 331 shown in FIG. 1).

In addition, when a wireless line is used instead of the wired cable 331, or when the wired cable 331 is used but the cable 331 does not need to be supported, and the like, a configuration in which the cable holding portions 221 and 222 are not provided may also be used.

<Combination Between Subject Fixing Body and Sensor Fixing Body>

In the present embodiment, the subject fixing body 21 and the sensor fixing body 22 are combined to form the measuring device 11.

As a specific example, while a member Q1 and a member Q2 of the sensor fixing body 22 shown in FIG. 2 are removed, and while the right hand rest 121 and the left hand rest 122 of the subject fixing body 21 shown in FIG. 2 are removed, the sensor fixing body 22 covers the subject fixing body 21 from the upper part to the lower part. Then, when the right hand rest 121 and the left hand rest 122 of the subject fixing body 21 are attached, the state of the measuring device 11 shown in FIG. 1 is obtained.

In the present embodiment, the right leg portion B1 and the left leg portion B2 of the sensor fixing body 22 are disposed outside in the lateral direction, and are disposed inside in the depth direction (in a direction of the front side and the back side) with respect to the right leg portion A1 and the left leg portion A2 of the subject fixing body 21.

In addition, lower surfaces of the right hand rest 121 and the left hand rest 122 of the subject fixing body 21 are disposed at an upper part of an upper surface of the platform portion B3 of the sensor fixing body 22.

Here, in the present embodiment, a configuration in which the subject fixing body 21 and the sensor fixing body 22 are directly detachable (separable and combinable) is shown, but the subject, fixing body 21 and the sensor fixing body 22 may also be configured to be, integrated and to be, inseparable.

In other words, the measuring device 11 may be configured as shown in FIG. 1, and the subject fixing body 21 and the sensor fixing body 22 may not necessarily have to be independently separated.

In the present embodiment, in the measuring device 11, the subject fixing body 21 and the sensor fixing body 22 do not come into contact with each other at any portion.

Figure 3:
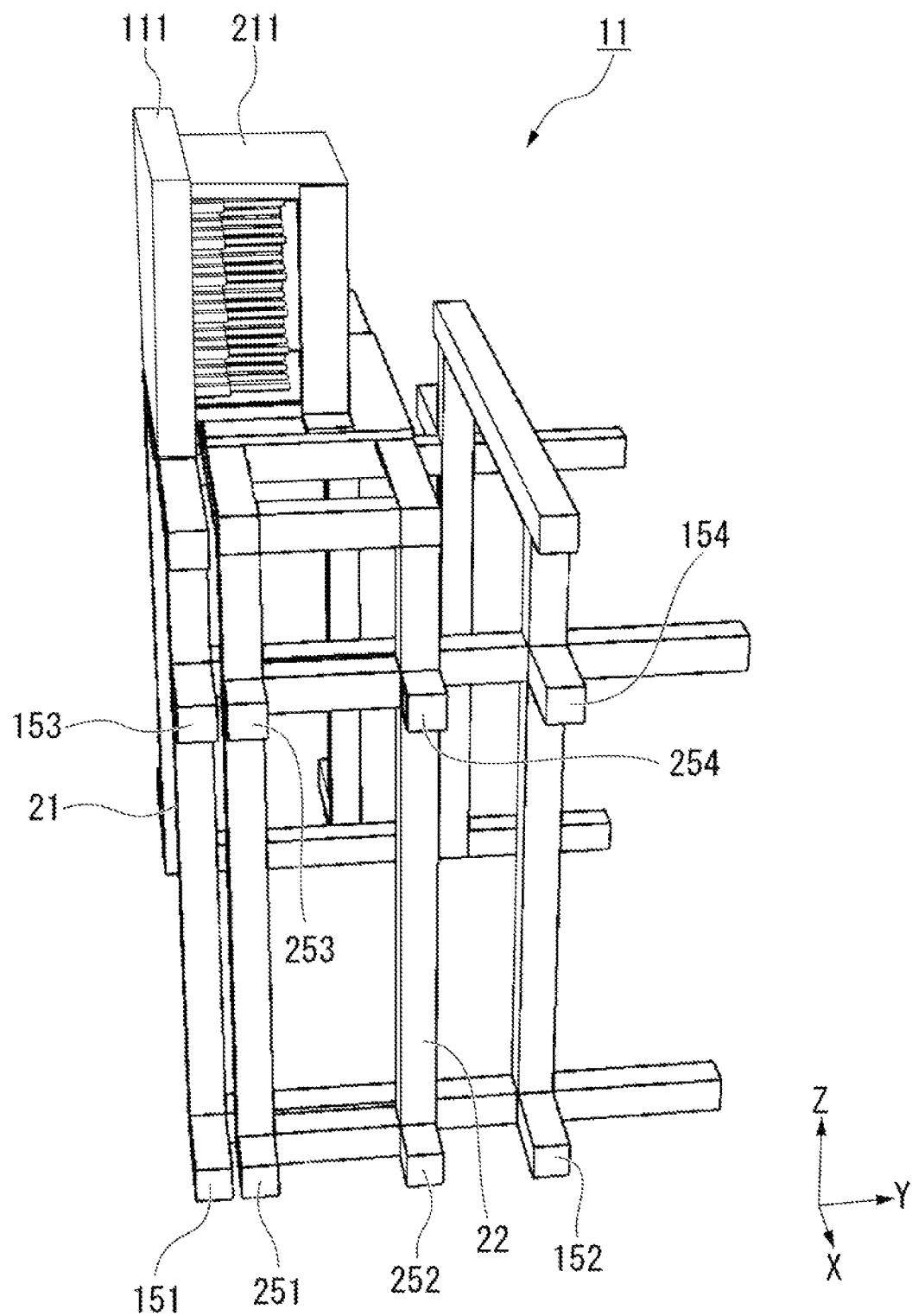
FIG. 3 is a diagram which shows a schematic configuration when the measuring device according to the first embodiment is viewed from a substantially left side.

FIG. 3 is a diagram which shows a schematic configuration when the measuring device 11 according to the first embodiment is viewed substantially from the left side.

For convenience of description, FIG. 3 shows an XYZ orthogonal coordinate system similar to that of FIG. 1.

Figure 4:
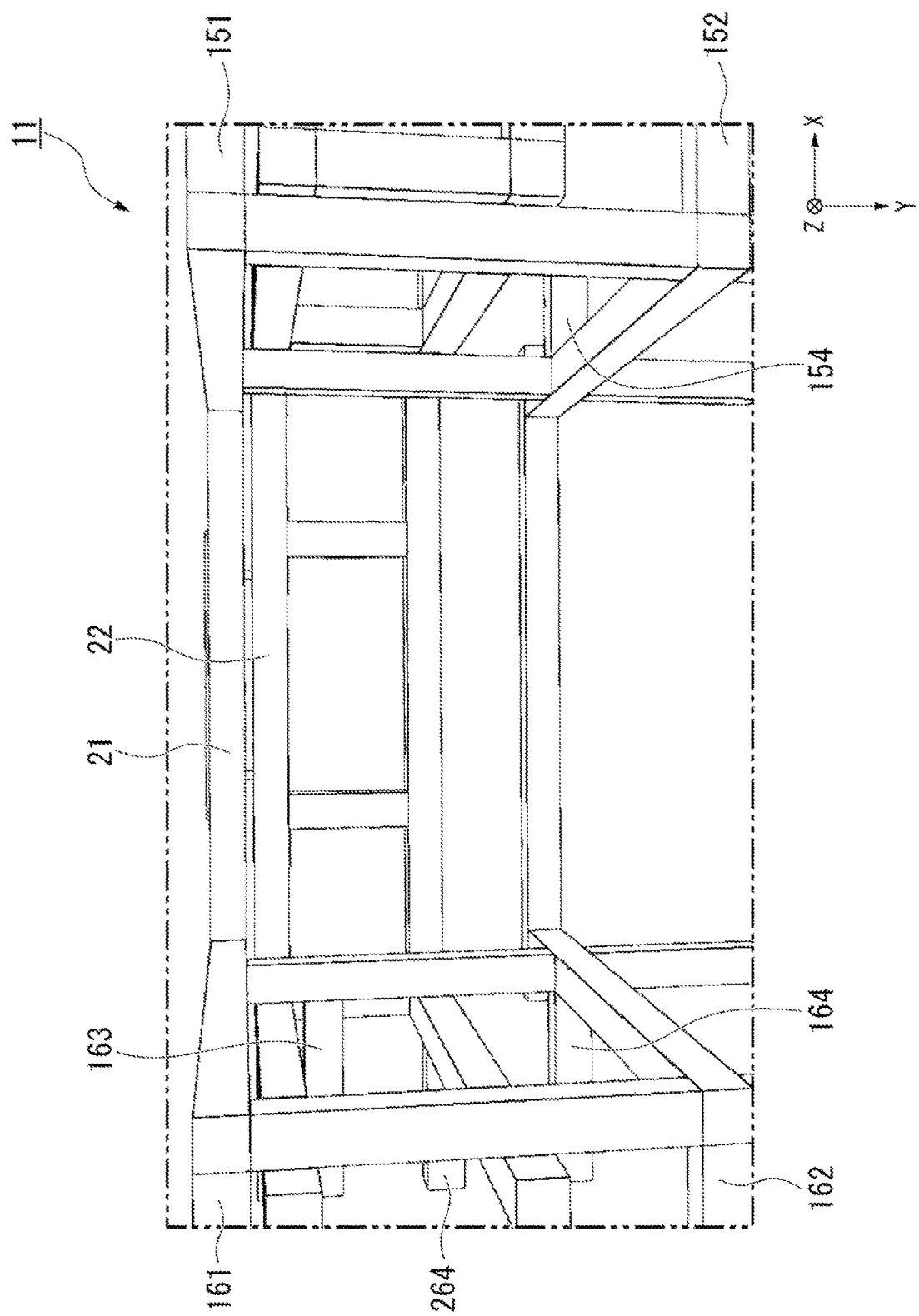
FIG. 4 is a diagram which shows a schematic configuration when the measuring device according to the first embodiment is viewed from a substantially bottom side.

FIG. 4 is a diagram which shows a schematic configuration when the measuring device 11 according to the first embodiment is viewed substantially from the bottom side.

For convenience of description, FIG. 4 shows an XYZ orthogonal coordinate system similar to that of FIG. 1.

Here, in FIGS. 3 and 4, some constituents (for example, the right hand rest 121, the left hand rest 122, the cable holding portions 221 and 222, and the like) are omitted to make, it easier to view the illustration.

<Example of Disposition of Sensor Holding Portion>

Figure 5:
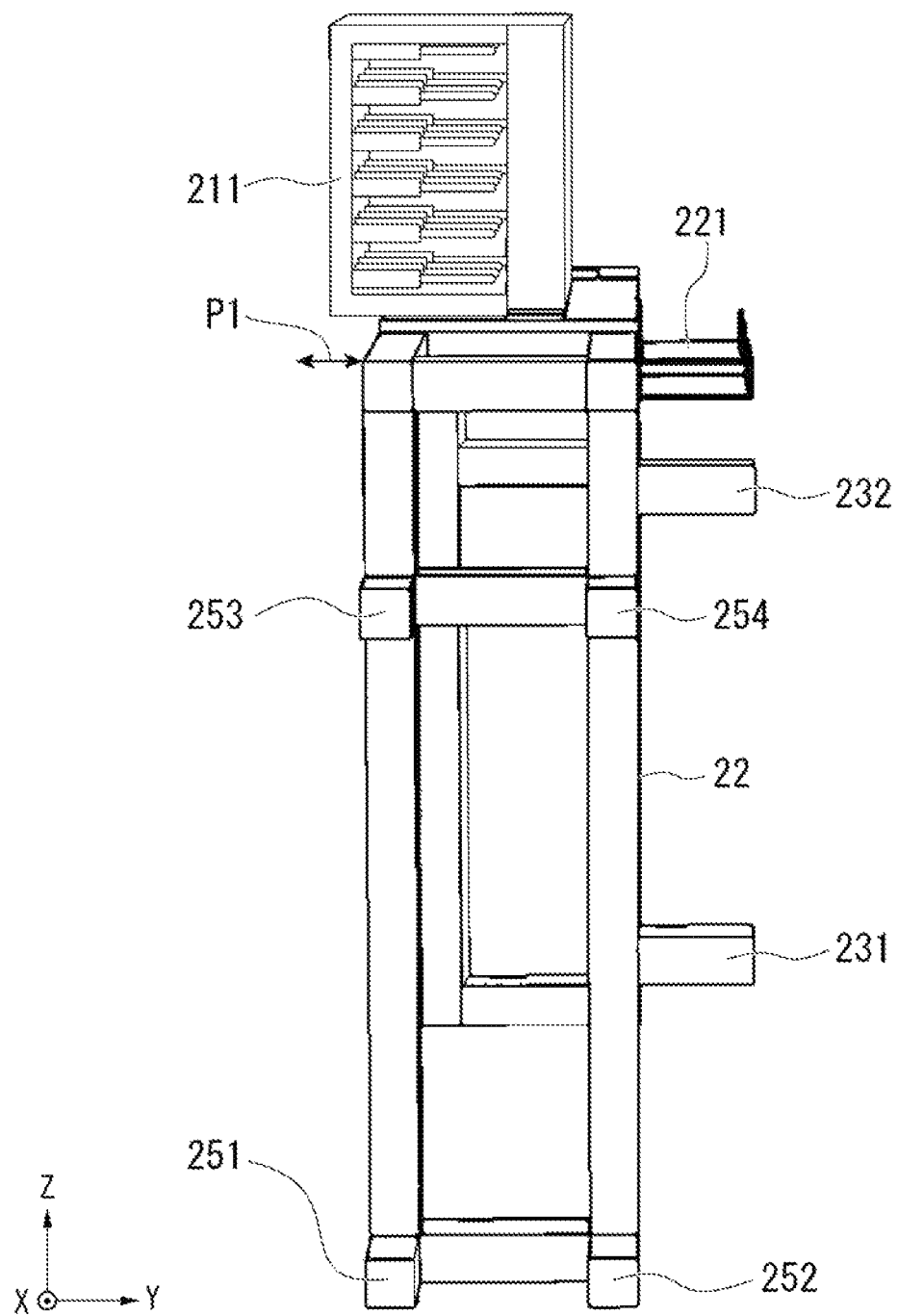
FIG. 5 is a diagram which shows an example of a disposition of a sensor holding portion of the subject fixing body of the measuring device according to the first embodiment.

FIG. 5 is a diagram which shows an example of disposition of the sensor holding portion 211 of the subject fixing body 21 of the measuring device 11 according to the first embodiment.

FIG. 5 shows a state of the measuring device 11 according to the first embodiment as viewed substantially from the right side.

For convenience of description, FIG. 5 shows an XYZ orthogonal coordinate system similar to that of FIG. 1.

In the present embodiment, surfaces on a front side of the right leg portion A1 and the left leg portion A2 of the subject fixing body 21 are parallel in the vertical direction.

Then, in the example of FIG. 5, the surface of the front side of the sensor holding portion 211 is disposed to protrude to the front side by a predetermined distance P1 from the surfaces on the front side of the right leg portion A1 and the left leg portion A2.

Note that the sensor holding portion 211 and the plate 111 are disposed so that they do not come into contact with each other in the state in which the subject fixing body 21 and the sensor fixing body 22 are combined.

<Example of Status of Measurement by Measuring Device>

Figure 6:
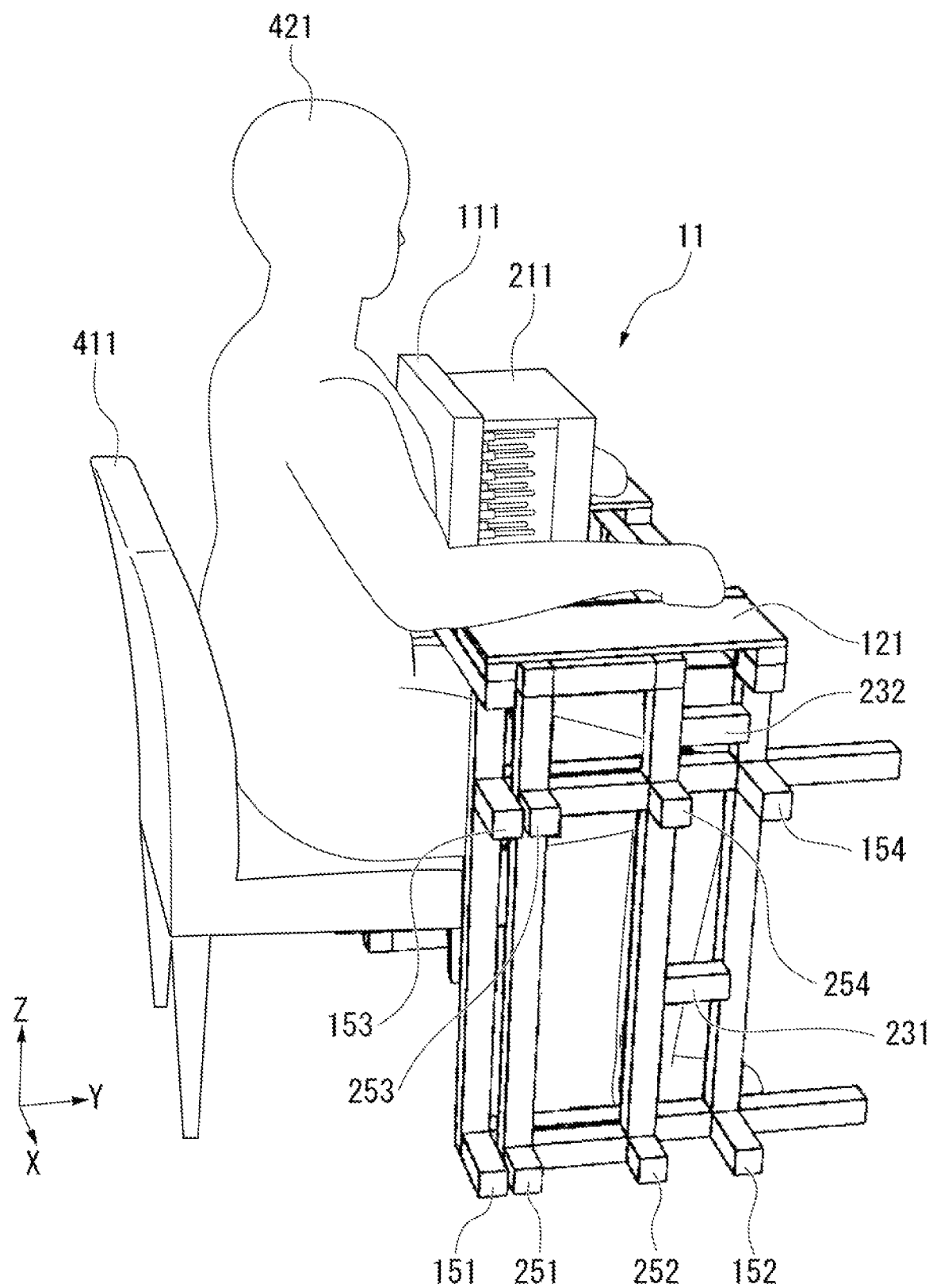
FIG. 6 is a diagram which shows an example of a status in which a subject (a person) is measured by the measuring device according to the first embodiment.

FIG. 6 is a diagram which shows an example of a status in which a subject (person) 421 is measured by the measuring device 11 according to the first embodiment.

For convenience of description, FIG. 6 shows an XYZ orthogonal coordinate system similar to that of FIG. 1.

FIG. 6 shows a chair 411, the subject 421, and an outline of the measuring device 11. The subject 421 is a person sitting on the chair 411.

The measurement is performed with a front surface of the subject 421 (a surface with the face) facing a surface on a front side of the measuring device 11 (a side with the plate 111).

The example of FIG. 6 shows a case in which the measuring device 11 measures information of a magnetic field (a magnetic signal) caused by movement of the heart of the subject 421.

A magnetic sensor is used as the sensor 311.

With the subject 421 sitting on the chair 411, the chest of the subject 421 faces an inside of the frame of the plate 111. For example, the measurement may be performed with the chest of the subject 421 being in contact with the surface of the front side of the plate 111.

The subject 421 can put a part of the right arm and the right hand thereof on an upper surface of the right hand rest 121, and similarly can put a part of the left arm and the left hand thereof on an upper surface of the left hand rest 122.

Even if the subject 421 comes into, contact with the subject fixing body 21, since the subject fixing body 21 and the sensor fixing body 22 do not come into contact, the sensor fixing body 22 does not move. As a result, in the measuring device 11, the measurement by the sensor 311 installed in the sensor fixing body 22 can be stably performed. In this manner, in the present embodiment, the subject fixing body 21 can assist the subject 421 in maintaining the posture.

In the present embodiment, the subject 421 is configured not to come into contact with the sensor fixing body 22 and the subject fixing body 21 is also configured not to come into contact with the sensor fixing body 22 when the measuring device 11 is performing measurement.

In this manner, in the present embodiment, the subject fixing body 21 and the sensor fixing body 22 are completely separated in terms of contact.

Note that the subject fixing body 21 and the sensor fixing body 22 may come into contact with each other except when the measuring device 11 is performing measurement.

Here, the chair 411 is not particularly limited, and, for example, a chair in which a height of a part (a seat surface) where the subject 421 sits is adjustable may be used, or a chair in which the height of the seat surface is fixed may also be used.

By using the chair in which the height of the seat surface is adjustable as the chair 411, it is possible to adjust a height relationship between the subject 421 and the sensor 311 (or the sensor holding portion 211).

<Measuring Device Including Measurement Room>

Figure 7:
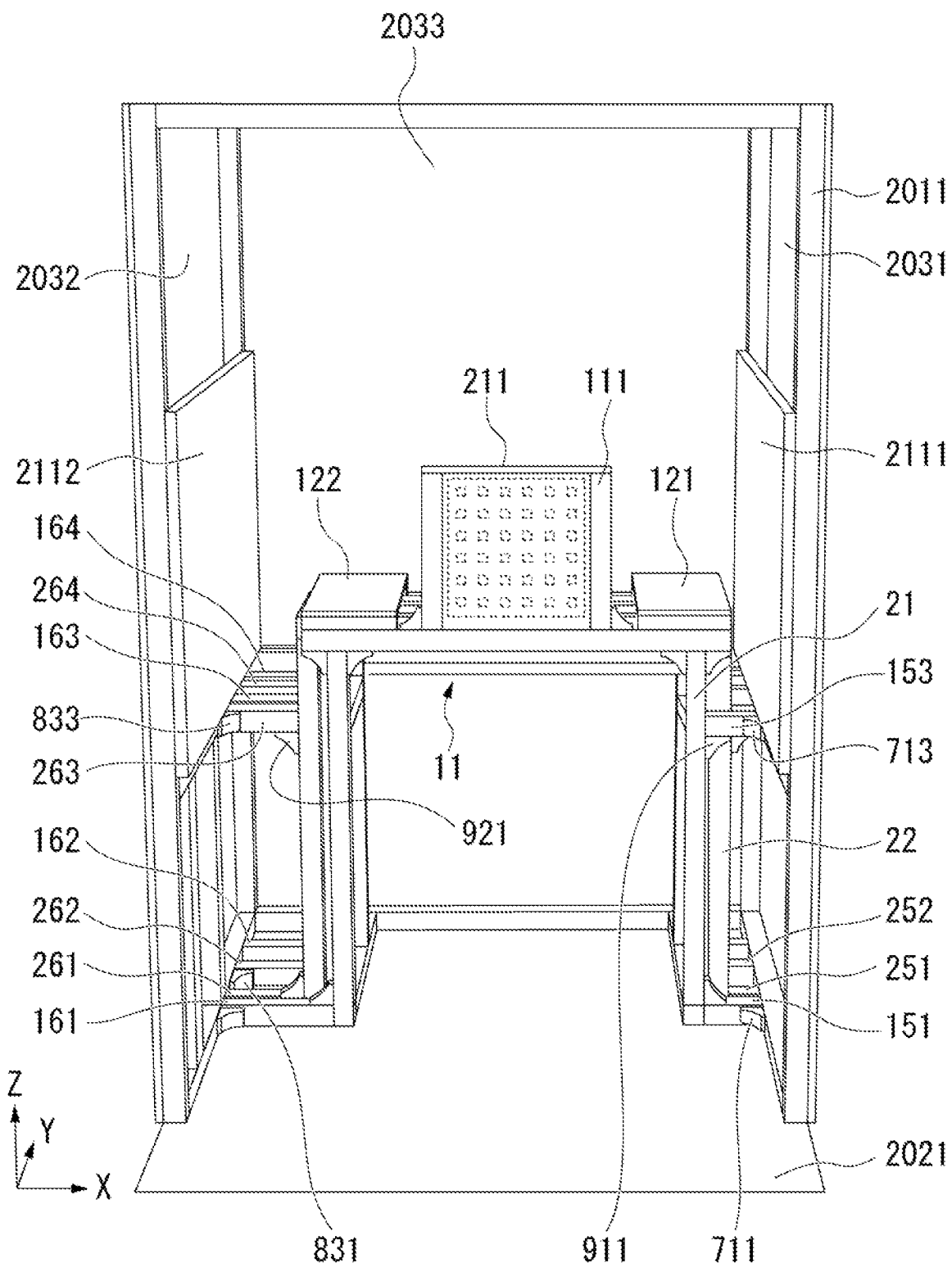
FIG. 7 is a diagram which shows an example of the measuring device including a measurement room according to the first embodiment.

FIG. 7 is a diagram which shows an example of the measuring device 11 including a measurement room 2011 according to the first embodiment.

For convenience of description, FIG. 7 shows an XYZ orthogonal coordinate system similar to that of FIG. 1.

In the present embodiment, the measurement room 2011 has a rectangular parallelepiped shape, and one of the six surfaces is open.

The measurement room 2011 includes a floor surface 2021 on the lower side, an upper ceiling surface 2022 on the upper side, a side wall surface 2031 on the right side, a side wall surface 2032 on the left side, and a back wall surface 2033 on the back side.

In the example of FIG. 7, a front side of the measurement room 2011 is open.

Here, in the example of FIG. 7, the floor surface 2021 and the upper ceiling surface 2022 are surfaces parallel to the XY plane, the two side wall surfaces 2031 and 2032 are surfaces parallel to the YZ plane, and the back wall surface 2033 is a surface parallel to the XZ plane, but is not limited to this.

Inside the measurement room 2011, the subject fixing body 21 and the sensor fixing body 22 that constitute the measuring device 11 are installed.

In the measurement room 2011, the subject fixing body 21 is disposed on the front side and the sensor fixing body 22 is disposed on the back, side.

The subject 421 enters through an opening of the measurement room 2011. Then, the measurement is performed by the measuring device 11 with the subject 421 positioned on the front side of the subject fixing body 21.

Here, although illustration of the chair 411 is omitted in FIG. 7, the measurement is performed by the measuring device 11 with the subject 421 sitting on the chair 411.

As another example, the measurement may be performed by the measuring device 11 with the subject 421 standing or the like without using the chair 411.

A plate-shaped shield 2111 is provided on a part of the side wall surface 2031 on the right side of the measurement room 2011. A surface of the shield 2111 is disposed parallel to the side wall surface 2031.

A plate-shaped shield 2112 is provided on a part of the side wall surface 2032 on the left side of the measurement room 2011. A surface of shield 2112 is disposed parallel to the side wall surface 2032.

The two shields 2112 are disposed at positions facing each other in the lateral direction.

For example, the two shields 2111 and 2112 are disposed in a portion that covers at least a position where the sensor 311 is disposed (the sensor holding portion 211 in the example of FIG. 7) in the lateral direction.

In the present embodiment, a magnetic sensor is used as the sensor 311, and a magnetic shield is used as each of the two shields 2111 and 2112.

When a sensor other than a magnetic sensor is used as the sensor 311, shields other than magnetic shields may be used as the shields 2111 and 2112 accordingly.

In addition, when the shields 2111 and 2112 are not necessary, the measurement room 2011 may not be provided with the shields 2111 and 2112.

A mode in which the subject fixing body 21 and the sensor fixing body 22 constituting the measuring device 11 are fixed to the measurement room 2011 will be described.

In the present embodiment, in the measuring device 11, the four protruding portions 151 to 154 of the right leg portion A1 of the subject fixing body 21 and the four protruding portions 251 to 254 of the right leg portion B1 of the sensor fixing body 22 are disposed to be in contact with the side wall surface 2031 on the right side of the measurement room 2011.

Moreover, in the present embodiment, in the measuring device 11, the four protruding portions 161 to 164 of the left leg portion A2 of the subject fixing body 21 and the four protruding portions 261 to 264 of the left leg portion B2 of the sensor, fixing body 22 are disposed to be in contact with the side wall surface 2032 on the left side of the measurement room 2011.

In addition, the subject fixing body 21, the sensor fixing body 22, and the measurement room 2011 are positioned using, for example, brackets. That is, the positions of the subject fixing body 21 and the sensor fixing body 22 in the measurement room 2011 are fixed.

In the example of FIG. 7, regarding the subject fixing body 21, a bracket 711 for fixing, the protruding portion 151 of the right leg portion A1 and the side wall surface 2031 on the right side, and a bracket 713 for fixing the protruding portion 153 of the right leg portion A1 and the side wall surface 2031 on the right side, and the like are shown.

Note that the example of FIG. 7 shows a case in which, regarding the subject fixing, body 21, a bracket (such, as a bracket 911) is used to, fix the two members that constitute the right leg portion A1.

Here, regarding the subject fixing body 21, a part of the right leg portion A1 has been described, but the same applies to other parts of the right leg portion A1 and the left leg portion A2.

In the example of FIG. 7, regarding the sensor fixing body 22, a bracket 831 that fixes the protruding portion 261 of the left leg portion B2 and the side wall surface 2032 on the left side, and a bracket 833 that fixes the protruding portion 263 of the left leg portion B2 and the side wall surface 2032 on the left side, and the like are shown.

Note that the example of FIG. 7 shows a case in which, regarding the sensor fixing body 22, a bracket (such as a bracket 921) is used to fix the two members that constitute the left leg portion B2.

Here, regarding the sensor fixing body 22, a part of the left leg portion B2 has been described, but the same applies to the other parts of the left leg portion B2 and the right leg portion B1.

Figure 8:
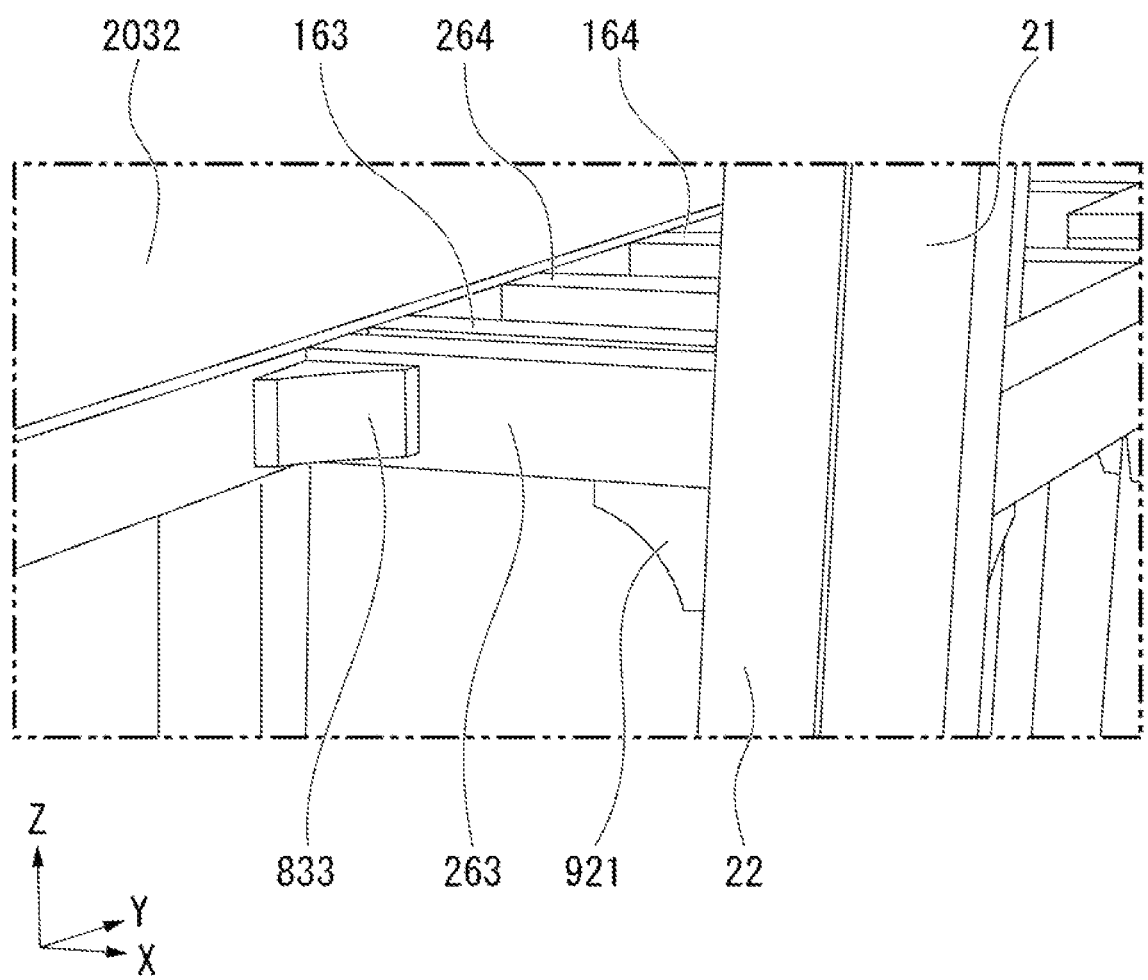
FIG. 8 is a diagram which shows an example of a mode in which the subject fixing body and the sensor fixing body are fixed to the measurement room in the first embodiment.

FIG. 8 is a diagram which shows an example of a mode in which the subject fixing body 21 and the sensor fixing body 22 are fixed to the measurement room 2011 in the first embodiment.

The example of FIG. 8 shows an example of the mode in which a part of the left leg portion B2 of the sensor fixing body 22 is fixed to the measurement room 2011 by enlarging it compared to the example of FIG. 7.

Here, in the present embodiment, a case in which a bracket is used as a fixture for positioning has been described, but as another example of fixing members to, each other, a mode in which only a screw is used without using a bracket to fix members to each other, a mode in which members are fixed to each other by adhesion or welding, or the like may also be used.

In addition, the examples of FIGS. 7 and 8 show a case in which the subject fixing, body 21 and the sensor fixing body 22 are fixed to each other using the side wall surface 2031 on the right side and the side wall surface 2032 on the left side of the measurement room 2011, but as another example, a configuration in which one or more of the floor surface 2021, the upper ceiling surface 2022, and the back wall surface 2033 of the measurement room 2011 are used to fix the measuring device 11 may also be used.

The measurement room 2011, the subject fixing body 21, and the sensor fixing body 22 may be configured to be, for example directly detachable (separable and combinable), or the measurement room 2011, the subject fixing body 21, and the sensor fixing body 22 may also be configured to be integrated and to be inseparable.

Here, in the example of FIG. 7, a case in which a dedicated box-shaped room having an opening is used as the measurement room 2011 is shown, but, for example, a room present in a building such as a normal building may also be used as the measurement room 2011. A shield or the like may be installed in the room.

In addition, in the present embodiment, as parts for fixing the subject fixing body 21 and the sensor fixing body 22 to the measurement room 2011, the subject fixing body 21 is provided with the protruding portions 151 to 154 and 161 to 164, and the sensor fixing body 22 is provided with the protruding portions 251 to 254 and 261 to 264, and various positions may be used as positions at which the respective protruding portions are provided.

For example, in the subject fixing body 21, when the right leg portion A1 is provided with one or more protruding portions and the left leg portion A2 is provided with one or more protruding portions, all of these protruding portions may be provided at positions that are bilaterally symmetrical, or some or all of these may be provided at positions that are not bilaterally symmetrical. For example, a configuration in which either the protruding portions disposed on the lower side of the right leg portion A1 and the left leg portion A2 or the protruding portions disposed on the upper side thereof are bilaterally symmetrical, and the others are bilaterally asymmetrical may be used.

Similarly, for example, in the sensor fixing body 22, when the right leg portion B1 is provided with one or more protruding portions and the left leg portion B2 is provided with one or more protruding portions, all of these protruding portions may be provided at positions that are bilaterally symmetrical, or some or all of these may be provided at, positions that are not bilaterally symmetrical. For example, a configuration in which either the protruding portions disposed on the lower side of the right leg portion B1 and the left leg portion B2 or the protruding portions disposed on the upper side thereof are bilaterally symmetrical, and the others are bilaterally asymmetrical may be used.

Note that when both the subject fixing body 21 and the sensor fixing body 22 are provided with protruding portions, the protruding portions of the subject fixing body 21 and the protruding portions of the sensor fixing body 22 are disposed not to interfere with each other (that is, to avoid being in the same position and colliding) in the state in which the subject fixing body 21 and the sensor fixing body 22 are combined.

In addition, in the present embodiment, a case in which, as parts for fixing the subject fixing body 21 and the sensor fixing body 22 to the measurement room 2011, the subject fixing body 21 is provided with the protruding portions 151 to 154 and 161 to 164, and the sensor fixing body 22 is provided with the protruding portions 251 to 254 and 261 to 264 is shown, but as another configuration example, some or all of these protruding portions may not be provided.

Here, in the present embodiment, a case in which the sensor holding portion 211 is provided on a top of the sensor fixing body 22 and the sensor 311 is held by the sensor holding portion 211 is shown, but as another configuration example, a configuration in which the sensor holding portion 211 is not provided may also be used.

In this configuration, for example, one or a plurality of sensors may be installed on the top of the platform portion B3 of the sensor fixing body 22, and the upper part of the platform portion B3 of the sensor fixing body 22 and the sensor may be fixed to each other by any fixture. For example, a screw, a fixing band, a single-sided or double-sided adhesive tape, a hook-and-loop fastener, an adhesive, or the like may be used as the fixture.

As described above, in the measurement system 1 according, to the present embodiment, the measuring device 11 can ensure a level of a measurement signal while curbing noise derived from the body movement of the subject 421.

The measuring device 11 according to the present embodiment includes the subject fixing body 21 that holds a posture of the subject 421, and the sensor fixing body 22 that fixes the sensor 311 for detecting a biological signal of the subject 421.

The subject fixing body 21 and the sensor fixing body 22 have separate structures.

Therefore, in the measuring device 11 according to the present embodiment, the subject 421 is not in contact with the sensor 311 (and the sensor holding portion 211), and the measurement can be performed with the body movement of the subject 421 not transmitted to the sensor 311 (and the sensor holding portion 211). As a result, the measuring device 11 can prevent the noise derived from the body movement of the subject 421 from being superimposed on a measurement result of a biological signal.

In addition, the measuring device 11 according to the present embodiment can perform measurement with the subject 421 and the sensor 311 brought closer to each other.

In addition, the measuring device 11 according to the present embodiment can easily maintain the posture of the subject 421.

In the measuring device 11 according to the present embodiment, the sensor fixing body 22 is provided with a sensor holding portion 211 that holds the sensor 311.

In addition, the sensor holding portion 211 has a mechanism for holding one or more sensors 311.

Therefore, in the measuring device 11 according to the present embodiment, the sensor 311 can be easily installed.

In the measuring device 11 according to the present embodiment, the subject fixing body 21 is provided with the plate 111 positioned between the subject 421 and the sensor 311.

Therefore, the measuring device 11 according to the present embodiment can prevent the subject 421 from being in contact with the sensor 311 (or the sensor holding portion 211). In addition, the measuring device 11 according to the present embodiment can enable the subject 421 to be measured in a comfortable posture.

In the measuring device 11 according to the present embodiment, the sensor holding portion 211 protrudes from an end portion of the sensor fixing body 22 (in the example of FIG. 5, an end portion on a negative side of an Y axis) to the plate 111 side. In addition, the sensor holding portion 211 is not in contact with the plate 111.

Therefore, in the measuring device 11 according to the present embodiment, it is possible to perform the measurement in a state in which the subject 421 and the sensor 311 are close to each other, thereby making it possible to acquire a large level of biological signal.

In the measuring device 11 according to the present embodiment, the subject fixing body 21 is provided with hand rests (the right hand rest 121, the left hand rest 122) on which the hands of the subject 421 are placed.

Therefore, the measuring device 11 according to the present embodiment can allow the subject 421 to place his or her hands on the hand rests during a measurement, and assist with the subject 421 in receiving the measurement in a stable posture.

In the measuring device 11 according to the present embodiment, the sensor fixing body 22 is provided with cable holding portions 221 and 222 that hold the cable 331 of the sensor 311.

Therefore, in the measuring device 11 according to the present embodiment, the cable 331 can be placed on the cable holding portions 221 and 222, and for example, the cable 331 of the sensor 311 can be prevented from being in contact with the feet of the subject 421.

In the measuring device 11 according to the present embodiment, one or both of the subject fixing body 21 and the sensor fixing body 22 (both of them in the present embodiment) are provided with fixtures for positioning (the protruding portions 151 to 154, the protruding portions 161 to 164, the protruding portions 251 to 254, the protruding portions 261 to 264 in the present embodiment).

Therefore, in the measuring device 11 according to the present embodiment, it is possible to fix the subject fixing body 21 or the sensor fixing body 22 at any place.

The measuring device 11 according to the present embodiment further includes the measurement room 2011. Then, one or both of the subject fixing body 21 and the sensor fixing body 22 (both of them in the example of FIG. 7) are fixed to one or both of the wall surface and the floor surface of the measurement room 2011 (the side wall surfaces 2031 and 2032 which are wall surfaces in the example of FIG. 7) by fixtures for positioning (the protruding portions 151 to 154, the protruding portions 161 to 164, the protruding portions 251 to 254, and the protruding portions 261 to 264 in the present embodiment).

Therefore, in the measuring device 11 according to the present embodiment, one or both of the subject fixing body 21 and the sensor fixing body 22 are fixed to the measurement room 2011 via the fixture for positioning, and thereby it is possible to prevent a positional relationship between one or both of the subject fixing body 21 and the sensor fixing body 22 and the measurement room 2011 from shifting.

Moreover, in the measuring device 11 according to the present embodiment, both the subject fixing body 21 and the sensor fixing body 22 are fixed to the measurement room 2011 via the fixture for positioning, and thereby it is possible to prevent the positional relationship between the subject fixing body 21 and the sensor fixing body 22 from shifting and to perform a stable measurement.

In the measuring device 11 according to the present embodiment, the sensor 311 is a magnetic sensor.

Therefore, the measuring device 11 according to the present embodiment can ensure the level of a measurement signal while curbing the noise derived from the body movement of the subject 421 when the biological signal is measured by the magnetic sensor.

Here, in general, the measurement results of the magnetic sensor are greatly influenced by vibration, but such influence can be curbed in the present embodiment.

In the present embodiment as an example of the biological signal of the subject 421, a case of an application to the measurement of a magnetic signal caused by an activity of the heart of the subject 421 is shown, but the biological signal is not particularly limited. It may be, for example, a signal related to the brain as well as the heart, and may be applied to an electrical signal as well as a magnetic signal.

Moreover, although a term "measurement" is used in the present embodiment, it may be called, for example, determination, detection, acquisition, or observation, instead of measurement.

Second Embodiment

In the present embodiment, the same constituents will be described with reference to FIGS. 9 and 10. For convenience of description, some of the components are omitted and the symbols of some of the components are omitted in some illustrations.

[Measurement System]

Figure 9:
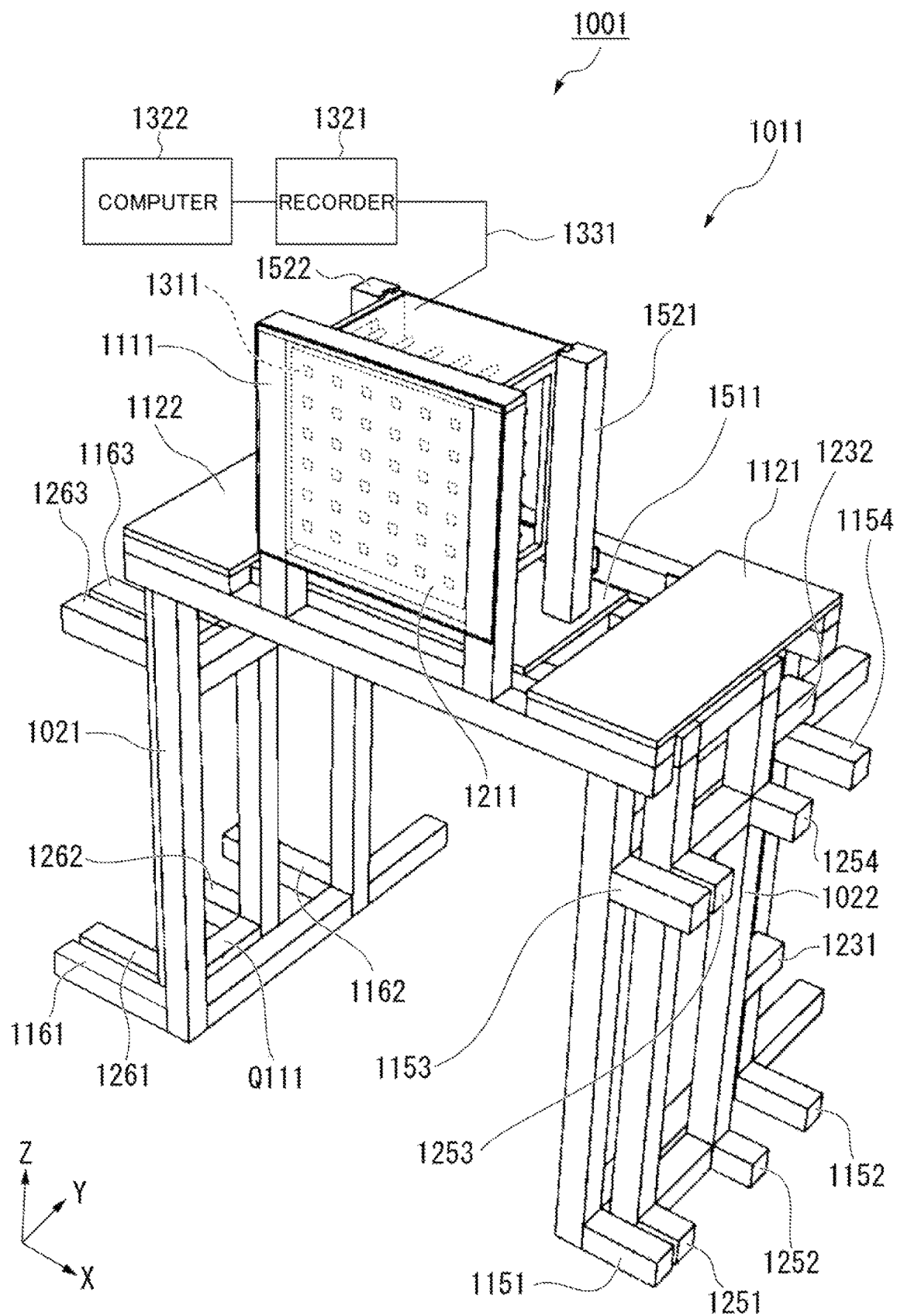
FIG. 9 is a diagram which shows a schematic configuration example of a measurement system including a measuring device according to a second embodiment.

FIG. 9 is a diagram which shows a schematic configuration example of a measurement system 1001 having a measuring device 1011 according to the second embodiment.

For convenience of description, FIG. 9 shows an XYZ orthogonal coordinate system, which is a three-dimensional orthogonal coordinate system. In the present embodiment, for convenience of description, the positive direction of the X-axis is the right direction, the negative direction of the X-axis is the left direction, the positive direction of the Y-axis is the backward direction, and the negative direction of the Y-axis is the forward direction, the positive direction of the Z-axis is the upward direction, and the negative direction of the Z-axis is the downward direction.

Here, the measurement system 1001 according to the present embodiment is schematically different from the measurement system 1 according to the first embodiment in that it can adjust the positions of the sensor holding portion 1211 of the sensor fixing body 1022 constituting the measuring device 1011, and is similar in other respects. For this reason, in the present embodiment, detailed description of the same points as in the first embodiment will be omitted.

The measurement system 1001 includes a measuring device 1011, a recorder 1321, a computer 1322, and a cable 1331.

Here, although one sensor 1311 attached to the measuring device 1011 is shown in the example of FIG. 9, a plurality of sensors may be attached to the measuring device 1011.

In the present embodiment, the recorder 1321, the computer 1322, the cable 1331, and the sensor 1311 are described as external apparatuses (devices) to the measuring device 1011, but as another example, one or more of the recorder 1321, the computer 1322, the cable 1331, and the sensors 1311 may be regarded to be included in the measuring device 1011.

<Measuring Device>

Figure 10:
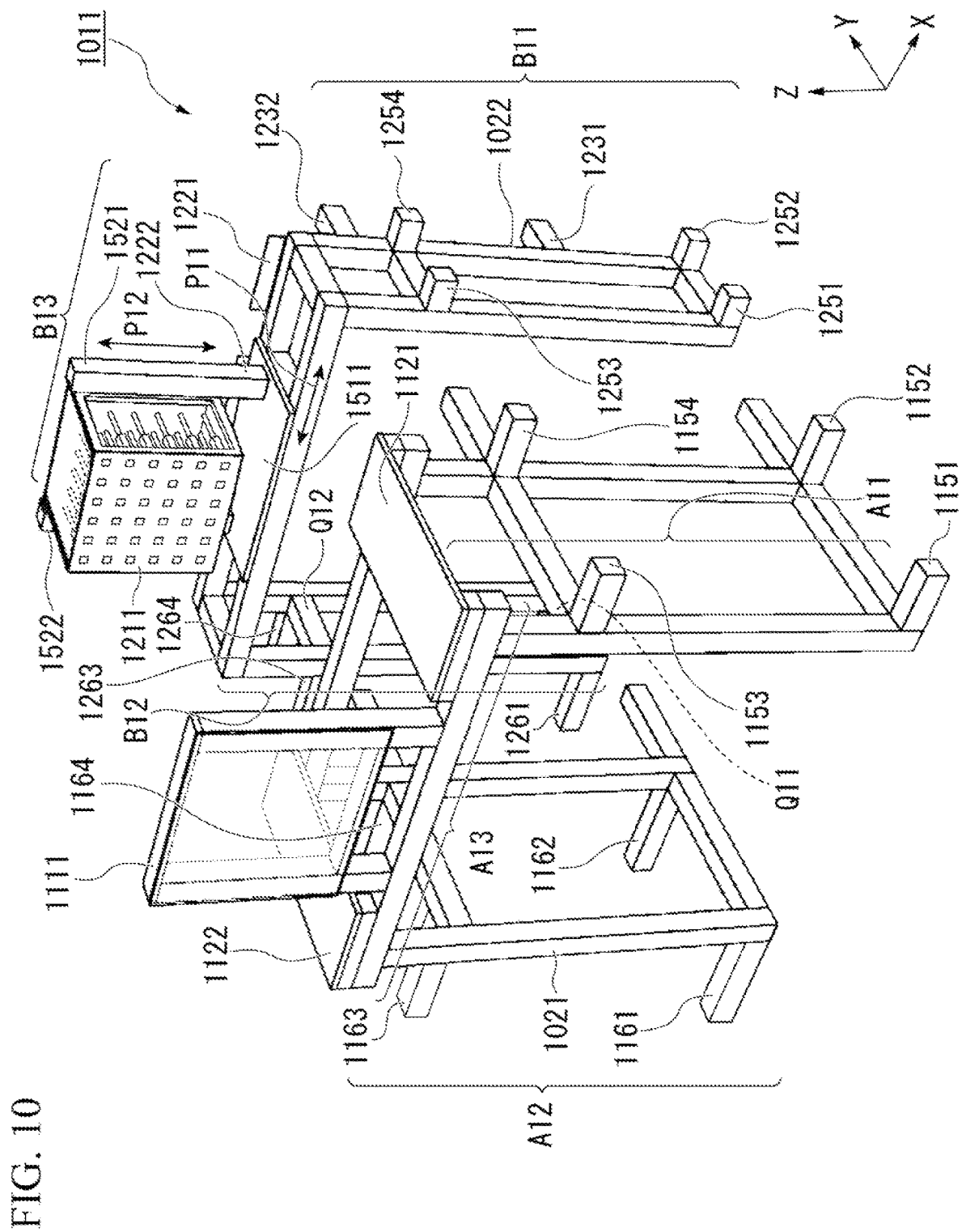
FIG. 10 is a diagram which shows a configuration example of each of a subject fixing body and a sensor fixing body constituting the measuring device according to the second embodiment.

FIG. 10 is a diagram which shows configuration examples of each of the subject fixing body 1021 and the sensor fixing body 1022 that constitute the measuring device 1011 according to the second embodiment.

For convenience of description, FIG. 10 shows an XYZ orthogonal coordinate system similar to that of FIG. 9.

Here, FIG. 9 shows a state in which the subject fixing body 1021 and the sensor fixing body 1022 are combined as a state when the measuring device 1011 is used.

On the other hand, FIG. 10 shows the subject fixing body 1021 and the sensor fixing body 1022 separately for convenience of description.

A configuration example of the subject fixing body 1021 will be described.

The subject fixing body 1021 includes a right leg portion A11, a left leg portion A12, and a platform portion A13.

The right leg portion A11 includes four protruding portions 1151 to 1154 that protrude to the right side.

The left leg portion A12 includes four protruding portions 1161 to 1164 that protrude to the left side.

The platform portion A13 includes a plate 1111, a right hand rest 1121, and a left hand rest 1122.

A configuration example of the sensor fixing body 1022 will be described.

The sensor fixing body 1022 includes a right leg portion B11, a left leg portion B12, and a platform portion B13.

The right leg portion B11 includes four protruding portions 1251 to 1254 that protrude to the right side.

The right leg portion B11 includes two protruding portions 1231 and 1232 that protrude to the back side.

In the present embodiment, detailed description of these two protruding portions 1231 and 1232 is omitted, but they may be used for positioning and the like.

The left leg portion B12 has four protruding portions 1261 to 1264 that protrude to the left side.

The platform portion B13 includes a component in which a plurality of rectangular parallelepiped members disposed on an upper surface of the right leg portion B11 and an upper surface of the left leg portion B12 are combined.

In addition, the platform portion B13 includes a position adjustment unit 1511 disposed on a top of the component, height adjustment units 1521 and 1522 disposed at an upper part of the position adjustment unit 1511, and a sensor holding portion 1211 attached to the height adjustment units 1521 and 1522.

In addition, the platform portion B13 includes two cable holding portions (cable receivers) 1221 and 1222 that protrude from the component to, the back side.

Here, a configuration of the sensor holding portion 1211 is, for example, the same as the configuration of the sensor holding portion 211 according to the first embodiment.

The position adjustment unit 1511 has a plate-like shape, and a plate-like surface is disposed parallel to an upper surface of the platform portion B13. The position adjustment unit 1511 has a mechanism capable of moving in the lateral direction (in a direction P11) on an upper side of the platform portion B13. The mechanism may be, for example, a rail-like mechanism extending in the lateral direction.

For example, a configuration may be used in which a movement of the position adjustment unit 1511 is manually performed by a person (person) who handles the measuring device 1011, or is electrically operated.

As an example, a configuration may be used in which a person directly comes into contact with the position adjustment unit 1511 to change a position of the position adjustment unit 1511.

As another example, a configuration may be used in which a handle or the like is provided on the platform portion B13 of the sensor fixing body 1022 or the like, and a person operates the handle or the like to change the position of the position adjustment unit 1511.

As still another example, a configuration may be used in which a switch is provided on the platform portion B13 of the sensor fixing body 1022 or the like, and a person operates the switch to change the position of the position adjustment unit 1511.

As still another example, a configuration may be used in which the computer 1322 and the position adjustment unit 1511 are connected in a communicative manner by wire or wirelessly and the computer 1322 controls a movement of the position adjustment unit 1511.

A configuration may be used in which the position adjustment unit 1511 and the platform portion B13 are screwed. For example, the platform portion B3 may be provided with a plurality of places where the position adjustment unit 1511 can be attached, and the position of the position adjustment unit 1511 may be changed by switching places where the position adjustment unit 1511 is attached among the plurality of places.

In the present embodiment as the position adjustment unit 1511 moves, the sensor holding portion 1211 also moves. As a result, a position of the sensor holding portion 1211 in the lateral direction can be adjusted.

In the present embodiment, the position adjustment unit 1511 has a function of adjusting the position in the lateral direction, but it may have, for example, a function of adjusting the position in the depth direction (a direction from the front side to the back side) or may have both functions.

The height adjustment units 1521 and 1522 each have a rectangular parallelepiped shape, and are disposed so that long sides of the rectangular parallelepiped shape extend upward from a surface of the position adjustment unit 1511.

The height adjustment unit 1521 on the right side and the height adjustment unit 1522 on the left side are disposed with a predetermined interval in the lateral direction. The sensor holding, portion 1211 is attached between the height adjustment unit 1521 on the right side and the height adjustment unit 1522 on the left side.

The height adjustment units 1521 and 1522 have a mechanism capable of moving the attached sensor holding portion 1211 in the vertical direction (a direction P12).

A configuration may be used in which the movement of the sensor holding portion 1211 by the height adjustment units 1521 and 1522 is performed manually by, for example, a person (person) handling the measuring device 1011 or is performed electrically.

As an example, a configuration may be used in which a person directly comes into contact with the height adjustment units 1521 and 1522 to change the position of the sensor holding portion 1211.

As another example, a configuration may be used in which a switch is provided on the platform portion B13 of the sensor fixing body 1022 or the like, and a person operates the switch and the position of the sensor holding portion 1211 is changed by the height adjustment units 1521 and 1522.

As still another example, a configuration may be used in which the computer 1322 and the height adjustment units 1521 and 1522 are connected in a communicative manner by wire or wirelessly, and the computer 1322 controls the movement of the sensor holding portion 1211 by the height adjustment units 1521 and 1522.

In the present embodiment, the sensor holding portion 1211 moves according to functions of the height adjustment units 1521 and 1522. As a result, the position of the sensor holding portion 1211 in the vertical direction (the height direction) can be adjusted.

<Combination of Subject Fixing Body and Sensor Fixing Body>

In the present embodiment, as in the first embodiment, the subject fixing body 1021 and the sensor fixing body 1022 are combined to form the measuring device 1011.

In the example of FIG. 10, regarding the sensor fixing body 1022, members Q11 and Q12 similar to the members Q1 and Q2 shown in FIG. 2 are shown.

Moreover, in the example of FIG. 9, a configuration example is shown in which a member Q111 is fitted at the lower end on the left side after the subject fixing body 1021 and the sensor fixing body 1022 are combined.

Note that the member Q111 may or may not be provided in the measuring device 1011.

In the present embodiment, in the measuring device 1011, the subject fixing body 1021 and the sensor fixing body 1022 do not come into contact with each other at any portion.

As described above, in the measurement system 1001 according to the present embodiment, the measuring device 1011 can ensure the level of a measurement signal while curbing the noise derived from the body movement of the subject 421.

In the measuring device 1011 according to the present embodiment, the sensor fixing body 22 includes the height adjustment units 1521 and 1522 that adjust a height of the sensor holding portion 211, and the position adjustment unit 1511 that adjusts a position in a direction (the lateral direction in the present embodiment) other than the height of the sensor holding portion 211.

Therefore, in the measuring device 1011 according to the present embodiment, for example, the height of the sensor 311 and the position other than the height can be adjusted according to the physique of the subject 421, a place at which a target biological signal is generated (for example, the heart, and the like), or the like.

Third Embodiment

The present embodiment shows a configuration example of a measuring device in which a reference sensor can be further attached to the measuring device 11 of the measurement system 1 shown in FIG. 1 according to the first embodiment. In addition, the reference sensor may be regarded as, for example, an external apparatus (device) to the measuring device, or may be regarded as being included in the measuring device.

In the present embodiment, for convenience of description, the same components as in the first embodiment will be denoted by the same symbols and described.

[Measurement System]

Figure 11:
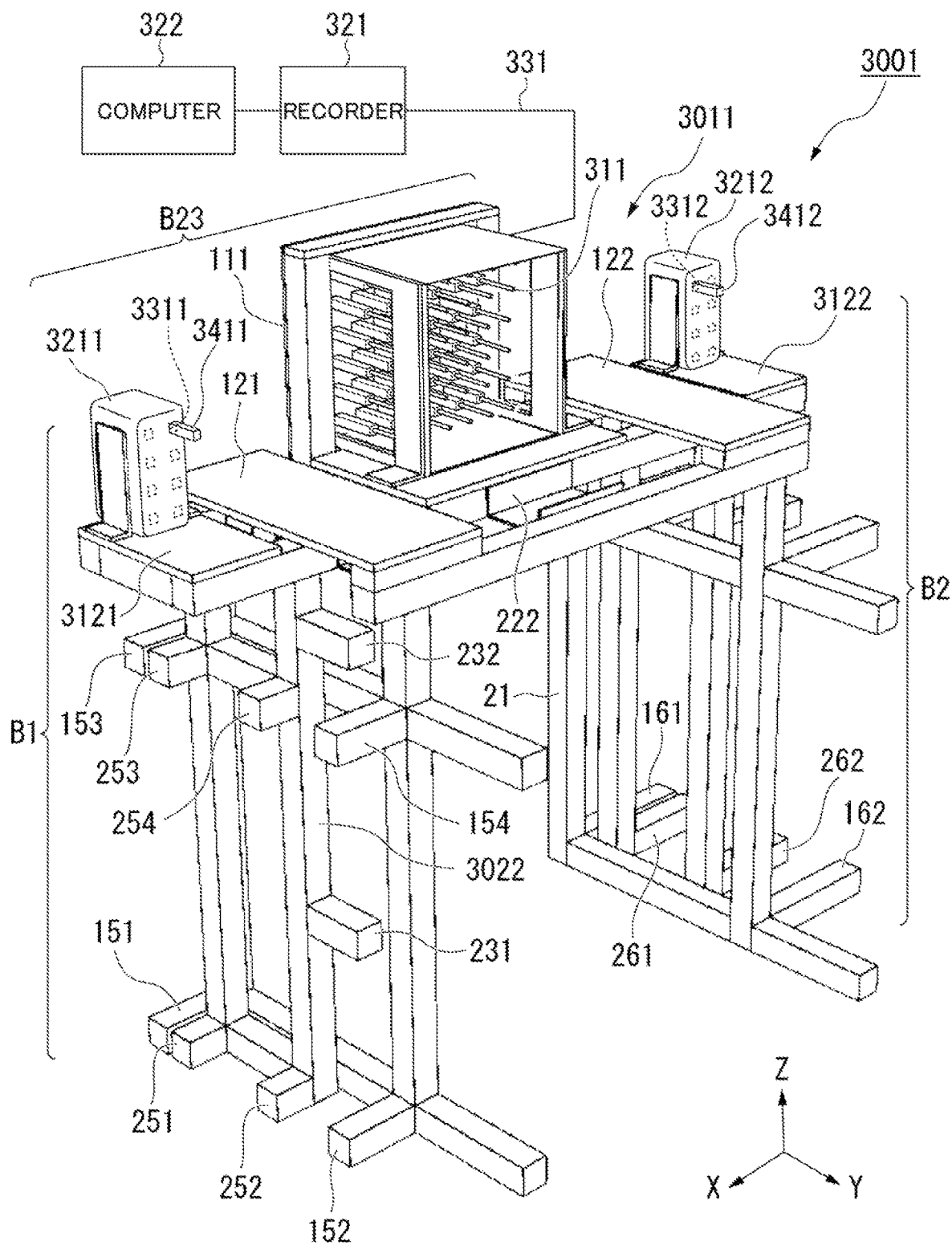
FIG. 11 is a diagram which shows a schematic configuration example of a measurement system including a measuring device according to a third embodiment.

FIG. 11 is a diagram which shows a schematic configuration example of a measurement system 3001 including a measuring, device 3011 according to a third embodiment.

For convenience of description, FIG. 11 shows an XYZ orthogonal coordinate system, which is a three-dimensional orthogonal coordinate system. In the present embodiment, for convenience of description, description will be made assuming that the positive direction of the X-axis is the right direction, the negative direction of the X-axis is the left direction, the positive direction of the Y-axis is the backward direction, the negative direction of the Y-axis is the forward direction, the positive direction of the Z-axis is the upward direction, and the negative direction of the Z-axis is the downward direction in the same manner as in FIG. 1.

The measurement system 3001 includes the measuring device 3011, the recorder 321, the computer 322, and the cable 331.

Here, configurations of the recorder 321, the computer 322, and the cable 331 are schematically the same as in the example of FIG. 1, and a detection signal (a reference signal) of the reference sensor is also processed in the present embodiment.

<Measuring Device>

FIG. 11 shows a state in which the subject fixing body 21 and the sensor fixing body 3022 are combined as a state when the measuring device 3011 is used.

The configuration of the subject fixing body 21 is similar to that shown in FIG. 1.

The sensor fixing body 3022 includes the right leg portion B1, the left leg portion B2, a platform portion B23, and reference sensor holding portions 3211 and 3212 that hold the reference sensor.

The reference sensor holding portion may also be called, for example, a reference sensor holding body.

Schematically, a configuration of the sensor fixing body 3022 is different from the configuration of the sensor fixing body 22 shown in FIGS. 1 and 2 in that it includes the platform portion B23 further extending laterally than the platform portion B3 shown in FIG. 2 and the reference sensor holding portions 3211 and 3212 disposed at an upper part of the platform portion B23, and is similar in other respects.

The platform portion B23 of the sensor fixing body 3022 includes a support portion 3121 on the right side and a support portion 3122 on the left side.

The support portion 3121 on the right side has a shape that supports the reference sensor holding portion 3211 on the right side disposed on the top thereof. In the present embodiment, the support portion 3121 has a planar shape perpendicular to the vertical direction, but other shapes may also be used.

The reference sensor holding portion 3211 on the right side has a rectangular parallelepiped shape. In the present embodiment, the reference sensor holding portion 3211 is disposed such that each, surface of the rectangular parallelepiped shape faces the upper side, the lower side, the left side, the right side, the front side, and the back side, respectively. Moreover, in the present embodiment, a surface on the upper side and a surface on the lower side are square surfaces, and the other surfaces are rectangular surfaces whose vertical direction is a longitudinal direction.

The reference sensor holding portion 3211 on the right side has a plurality of holes to which the reference sensor can be attached on a surface on the back side.

In the example of FIG. 11, four holes are arranged at predetermined intervals in the vertical direction, two holes are arranged at predetermined intervals in the horizontal direction on the surface, and thus there are eight holes in total, but only one hole 3311 is denoted by a symbol for convenience of illustration.

In addition, in the example of FIG. 11, only one reference sensor 3411 attached by being inserted into the hole 3311 is shown, but reference sensors may be attached to any number of holes.

Note that any mode may also be used as a shape of the reference sensor holding portion 3211, a mechanism of an attachment portion (a hole in the present embodiment) to which each reference sensor is attached, a position where the mechanism is provided, the number of the mechanisms, and the like.

For example, in the present embodiment, the reference sensor holding portion 3211 is a constituent that can attach a plurality of reference sensors thereto, but as another example, a constituent that can attach only one reference sensor thereto may also be used.

In addition, in the present embodiment, the reference sensor holding portion 3211 is a constituent that can attach or detach a reference sensor, but as another example, the reference sensor holding portion 3211 and the reference sensor may be configured to be integrated.

In the present embodiment, configurations of the support portion 3122 on the left side, the reference sensor holding portion 3212 on the left side, and the hole 3312 are bilaterally symmetrical to configurations of the support portion 3121 on the right side, the reference sensor holding portion 3211 on the right side, and the hole 3311, respectively. Note that a configuration that is not bilaterally symmetrical between the right side and the left side may also be used.

As described above, in the measurement system 3001 according to the present embodiment, the measuring device 3011 can ensure the level of a measurement signal while curbing the noise derived from the body movement of the subject.

In the measuring device 3011 according to the present embodiment, for example, the reference sensor holding portions 3211 and 3212 arrange one or more reference sensors that acquire an environmental signal that does not include a signal of interest (a biological signal in the present embodiment), and thereby it is possible to apply environmental noise removal, and as a result, an effect of curbing the noise can be enhanced.

Here, in the measuring device 3011 according to the present embodiment, each reference sensor measures (detects) a reference signal to curb noise superimposed on a biological signal detected by a measurement sensor.

The reference signal is used, for example, to remove the noise component contained in the biological signal detected by the measurement sensor (the sensor 311 as in the first embodiment in the present embodiment). As an example, the reference sensor detects a signal caused by an environment other than a living body as a reference signal when the measurement sensor detects a biological signal. As an example, when a magnetic signal caused by a living body is used as a signal of interest, a magnetic signal caused by an environmental magnetic field may be used as the reference signal.

In the present embodiment, there is no particular limitation on arithmetic processing using the biological signal detected by the measurement sensor and the reference signal detected by the reference sensor, and arbitrary arithmetic processing may be executed.

Such arithmetic processing is executed, for example, by an arithmetic device such as a computer (the computer 322 in the present embodiment).

In the measuring device 3011 according to the present embodiment, for example, to reduce environmental noise, it is possible to reduce environmental noise by signal processing such as adaptive noise cancelling (ANC) using a reference sensor.

Although illustration is omitted in the example of FIG. 11, for example, each reference sensor may transmit information on a result of the measurement to the recorder 321 via a wired cable or wirelessly. In this case, the recorder 321 can store the information and the computer 322 can process the information.

Here, in the present embodiment, an example of a configuration in which the sensor fixing body 3022, the support portions 3121 and 3122, and the reference sensor holding portions 3211 and 3212 are integrated is shown, but the present invention is not limited to this, and other configurations may also be used.

For example, in the present embodiment, a case in which a configuration related to the reference sensor is applied to a configuration of the first embodiment is shown, but the configuration related to the reference sensor may also be applied to a configuration of the second embodiment.

Fourth Embodiment

The present embodiment shows a configuration example of a measuring device in which a reference sensor can be further attached to the measuring device 11 of the measurement system 1 shown in FIG. 1 according to the first embodiment. Note that the reference sensor may be regarded as, for example, an external apparatus (device) to the measuring device, or may be regarded as being included in the measuring device.

In the present embodiment, for convenience of description, the same components as in the first embodiment will be denoted by the same symbols and described.

[Measurement System]

Figure 12:
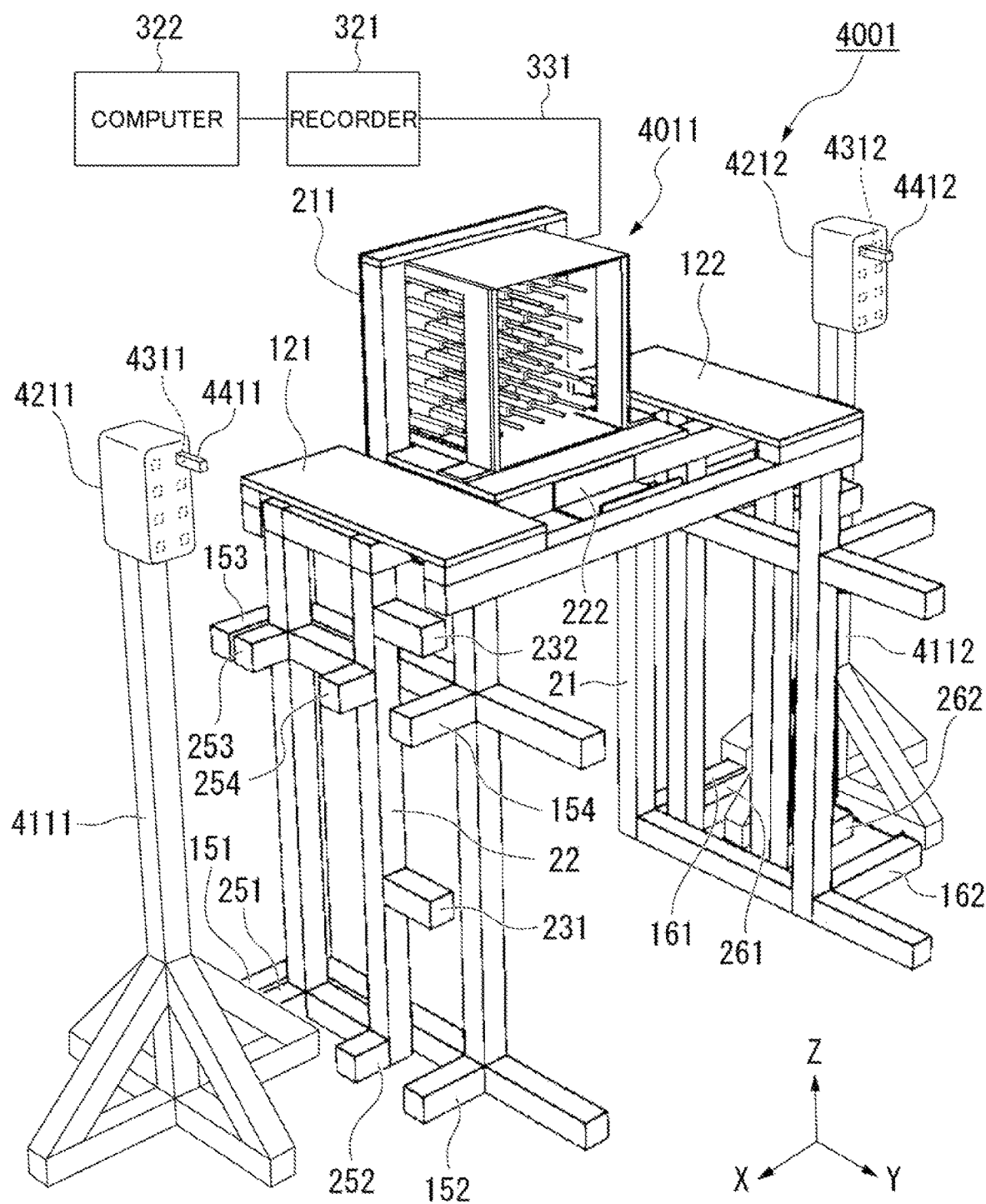
FIG. 12 is a diagram which shows a schematic configuration example of a measurement system including a measuring device according to a fourth embodiment.

FIG. 12 is a diagram which shows a schematic configuration example of a measurement system 4001 including a measuring device 4011 according to a fourth embodiment.

For convenience of description, FIG. 12 shows an XYZ orthogonal coordinate system, which is a three-dimensional orthogonal coordinate system. In the present embodiment, for convenience of description, description will be made assuming that the positive direction of the X-axis is the right direction, the negative direction of the X-axis is the left direction, the positive direction of the Y-axis is the backward direction, the negative direction of the Y-axis is the forward direction, the positive direction of the Z-axis is the upward direction, and the negative direction of the Z-axis is the downward direction in the same manner as in FIG. 1.

The measurement system 4001 includes the measuring device 4011, the recorder 321, the computer 322, and the cable 331.

Here, configurations of the recorder 321, the computer 322, and the cable 331 are schematically the same as, in the example of FIG. 1, and a detection signal (a reference signal) of the reference sensor is also processed in the present embodiment.

<Measuring Device>

The measuring device 4011 includes the subject fixing body 21, the sensor fixing body 22, a reference sensor support portion 4111 and a reference sensor holding portion 4211 on the right side, and a reference sensor support portion 4112 and a reference sensor holding portion 4212 on the left side.

The reference sensor holding portion may be called, for example, the reference sensor holding body.

FIG. 12 shows a state in which the subject fixing body 21 and the sensor fixing body 22 are combined as a state when the measuring device 4011 is used.

The configurations of the subject fixing body 21 and the sensor fixing body 22 are similar to those shown in FIG. 1.

In addition, in FIG. 12, as a state when the measuring device 4011 is used, a state in which the reference sensor support portion 4111 and the reference sensor holding portion 4211 on the right side, and the reference sensor support portion 4112 and the reference sensor holding portion 4212 on the left side are installed near the subject fixing body 21 and the sensor fixing body 22 is shown.

In the example of FIG. 12, the reference sensor support portion 4111 and the reference sensor holding portion 4211 on the right side and the reference sensor support portion 4112 and the reference sensor holding portion 4212 on the left side are disposed without being in contact with the subject fixing body 21 and the sensor fixing body 22.

The reference sensor support portion 4111 on the right side has a shape that supports the reference sensor holding portion 4211 on the right side, disposed on a top thereof.

In the present embodiment, the reference sensor support portion 4111 has a base portion disposed at the lower part and a bar-shaped portion extending upward from the base portion, and is a constituent that supports the reference sensor holding, portion 4211 disposed at the upper part of the bar-shaped portion, but other constituents may also be used.

The reference sensor holding portion 4211 on the right side has a rectangular parallelepiped shape. In the present embodiment, the reference sensor holding portion 4211 is disposed such that each surface of the rectangular parallelepiped shape faces the upper side, the lower side, the left side, the right side, the front side, and the back side, respectively. Moreover, in the present embodiment, a surface on the upper side and a surface on the lower side are square surfaces, and the other surfaces are rectangular surfaces whose vertical direction is a longitudinal direction.

The reference sensor holding portion 4211 on the right side has a plurality of holes to which the reference sensor can be attached on a surface on the back side.

In the example of FIG. 12, four holes are arranged at predetermined intervals in the vertical direction, two holes are arranged at predetermined intervals in the lateral direction on the surface, and thus there are eight holes in total, but only one hole 4311 is denoted by a symbol for convenience of illustration.

In addition, in the example of FIG. 12, only one reference sensor 4411 attached by being inserted into the hole 4311 is shown, but reference sensors may be attached to any number of holes.

Note that any mode may also be used as a shape of the reference sensor holding portion 4211, a mechanism of an attachment portion (a hole in the present embodiment) to which each reference sensor is attached, a position where the mechanism is provided, the number of the mechanisms, and the like.

For example, in the present embodiment, the reference sensor holding portion 4211 is a constituent that can attach a plurality of reference sensors thereto, but as another example, a constituent that can attach only one reference sensor thereto may also be used.

In addition, in the present embodiment, the reference, sensor holding portion 4211 is a constituent that can attach or detach a reference sensor, but as another example, the reference sensor holding portion 4211 and the reference sensor may be configured to be integrated.

Moreover, in the present embodiment, the reference sensor support portion 4111 and the reference sensor holding portion 4211 may be, for example, constituents that can be attachable or detachable to or from each other, or may be configured to be integrated.

In the present embodiment, configurations of the reference sensor support portion 4112 on the left side, the reference sensor holding portion 4212 on the left side, and the hole 4312 are bilaterally symmetrical to configurations of the reference sensor support portion 4111 on the right side, the reference sensor holding portion 4211 on the right, side, and the hole 4311, respectively. Note that a configuration that is not bilaterally symmetrical between the right side and the left side may also be used.

As described above, in the measurement system 4001 according to the present embodiment, the measuring device 4011 can ensure the level of a measurement signal while curbing the noise derived from the body movement, of the subject.

In the measuring device 4011 according to the present embodiment, for example, the reference sensor holding portions 4211 and 4212 arrange one or more reference sensors that acquire an environmental signal that does not include a signal of interest (a biological signal in the present embodiment), and thereby it is possible to apply environmental noise removal, and as a result, the effect of curbing the noise can be enhanced.

Here, in the measuring device 4011 according to the present embodiment, each reference sensor measures (detects) a reference signal to curb noise superimposed on a biological signal detected by the measurement sensor.

The reference signal is used, for example, to remove the noise component contained in the biological signal detected by the measurement sensor (the sensor 311 as in the first embodiment in the present embodiment). As an example, the reference sensor detects a signal caused by an environment other than a living body as a reference signal when the measurement sensor detects a biological signal. As an example, when a magnetic signal caused by a living body is used as a signal of interest, a magnetic signal caused by an environmental magnetic field may be used as the reference signal.

In the present embodiment, there is no particular limitation on arithmetic processing, using the biological signal detected by the measurement sensor and the reference signal detected by the reference sensor, and arbitrary arithmetic processing may be executed.

Such arithmetic processing is executed, for example, by an arithmetic device such as a computer (the computer 322 in the present embodiment).

In the measuring device 4011 according to the present embodiment, for example, to reduce environmental noise, it is possible to reduce environmental noise by signal processing such as adaptive noise cancelling (ANC) using a reference sensor.

Although illustration is omitted in the example of FIG. 12, for example, each reference sensor may transmit information on a result of the measurement to the recorder 321 via a wired cable or wirelessly. In this case, the recorder 321 can store the information and the computer 322 can process the information.

Here, in the present embodiment, an example of a configuration in which the reference sensor support portions 4111 and 4112 and the reference sensor holding portions 4211 and 4212 are separate bodies, independent from the sensor fixing body 22, is shown, but the present invention is not limited to this, and other configurations may also be used.

For example, in the present embodiment, a case in which a configuration related to the reference sensor is applied to a configuration of the first embodiment is shown, but the configuration related to the reference sensor may also be applied to a configuration of the second embodiment.

Note that a program for realizing a function of any component in any device described above may be recorded on a computer-readable recording medium, and the program may be read and executed by a computer system. The term compute system as used herein includes an operating system or hardware such as peripheral devices. In addition, "computer-readable recording medium" refers to a portable medium such, as a flexible disc, a magneto-optical disc, a ROM, a compact disc (CD)-read only memory (ROM), and a storage device such as a hard disk embedded in the computer system. Furthermore, "computer-readable recording medium" is assumed to include a medium that holds a program for a certain period of time, like a volatile memory inside a computer system that serves as a server or a client when a program is transmitted via a network such as the Internet or a communication line such as a telephone line. The volatile memory may be, for example, a random access memory (RAM). The recording medium may be, for example, a non-transitory recording medium.

In addition, the program described above may be transmitted, from a computer system storing this program in a storage device or the like to another computer system via a transmission medium or by transmission waves in a transmission medium. Here, the "transmission medium" for transmitting the program refers to a medium having a function of transmitting information, like a network such as the Internet or a communication line such as a telephone line.

In addition, the program described above may be for realizing a part of the functions described above. Furthermore, the program described above may be a so-called difference file, which can realize the functions described above in combination with a program already recorded in the computer system. A difference file may be called a difference program.

In addition, the function of any component in any device described above may be realized by a processor. For example, each processing in the embodiments may be realized by a processor that operates based on information such as a program, and a computer-readable recording medium that stores the information such as the program. Here, in the processor, for example, a function of each part may be realized by separate pieces of hardware, or the function of each part may be realized by integrated hardware. For example, the processor includes hardware, and the hardware may include at least one of circuits that process digital signals and circuits that process analog signals. For example, the processor may be configured using one or both of one or more circuit devices and one or more circuit elements mounted on a circuit board, An integrated circuit (IC) or the like may be used as the circuit device, and a resistor, a capacitor, or the like may be used as the circuit element.

Here, the processor may also be, for example, a CPU. However, the processor is not limited to the CPU, and various processors such as a graphics processing unit (GPU) and a digital signal processor (DSP) may also be used. In addition, the processor may be, for example, a hardware circuit based on an application specific integrated circuit (ASIC). Moreover, the processor may be configured from, for example, a plurality of CPUs. or may also be configured from a plurality of ASIC hardware circuits. Moreover, the processor may be configured from, for example, a combination of a plurality of CPUs and the plurality of ASIC hardware circuits. Moreover, the processor may include, for example, one or more of an amplifier circuit, a filter circuit, and the like for processing analog signals.

Although the embodiments of the present invention have been described in detail with reference to the drawings, a specific configuration is not limited to the present embodiments, and includes design and the like within a range not departing from the gist of the present invention.

[Appendix]

(Configuration example 1) to (Configuration example 12) are shown.

Configuration Example 1

A measuring device includes a first, fixing body, a sensor fixing body configured to fix a sensor for detecting a biological signal, and the sensor, in which the first fixing body and the sensor fixing body have separate structures.

Configuration Example 2

The measuring device according to (Configuration example 1) further includes a sensor holding portion configured to hold the sensor in the sensor fixing body, in which the sensor holding portion has a mechanism that holds one or more sensors.

Configuration Example 3

The measuring device according to (Configuration example 1) or (Configuration example 2) in which the first fixing body is provided with a plate disposed at a position corresponding to the sensor.

Here, the plate is positioned between the subject and the sensor during measurement.

Configuration Example 4

The measuring device according to (Configuration example 2) in which the first fixing body is provided with a plate disposed at a position corresponding to the sensor, the sensor holding portion protrudes from an end portion of the sensor fixing body to a side of the plate, and the sensor holding portion is not in contact with the plate.

Configuration Example 5

The measuring device according to (Configuration example 2) or (Configuration example 4) in which the sensor fixing body, is provided with a height adjustment unit that adjusts a height of the sensor holding portion and a position adjustment unit that adjusts a position in a direction of the sensor holding portion other than the height.

Configuration Example 6

The measuring device according to any one of (Configuration example 1) to (Configuration Example 5) further includes a stand above the first fixing body.

Here, for example, the stand is a hand rest on which a hand of the subject is placed.

Configuration Example 7

The measuring device according to any one of (Configuration example 1) to (Configuration example 6) in which the sensor fixing body is provided with a cable holding portion that holds a cable of the sensor.

Configuration Example 8

The measuring device according to any one of (Configuration example 1) to (Configuration example 7) in which one or both of the first fixing body and the sensor fixing body are provided with a fixture for positioning.

Configuration Example 9

The measuring device according to (Configuration example 8) further includes a measurement room, in which one or both of the first fixing body and the sensor fixing body is fixed to one or both of a wall surface and a floor surface of the measurement room by the fixture for positioning.

Configuration Example 10

The measuring device according to any one of (Configuration example 1) to (Configuration example 9) in which the sensor is a magnetic sensor.

Configuration Example 11

The measuring device according to any one of (Configuration example 1) to (Configuration example 10) in which the first fixing body is a subject fixing body that holds a posture of a subject, and the sensor is a sensor that detects the biological signal of the subject.

Configuration Example 12

The measuring device according to any one of (Configuration example 1) to (Configuration example 11) further includes a reference sensor configured to detect a reference signal to curb noise that is superimposed on the biological signal detected by the sensor, and a reference sensor holding portion configured to hold the reference sensor.

EXPLANATION OF REFERENCES 1, 1001, 3001, 4001 Measurement system
11, 1011, 3011, 4011 Measuring device
21, 1021 Subject fixing body
22, 1022, 3022 Sensor fixing body
111, 1111 Plate
121, 1121 Right hand rest
122, 1122 Left hand rest
151 to 154, 161 to 164, 231, 232, 251 to 254, 261 to 264, 1151 to 1154, 1161 to 1164, 1231, 1232, 1251 to 1254, 1261 to 1264 Protruding portion
211, 1211 Sensor holding portion
221, 222 1221, 1222 Cable holding portion
311, 1311 Sensor
321, 1321 Recorder
322, 1322 Computer
331, 1331 Cable
411 Chair
421 Subject
711, 713, 831, 833, 911, 921 Bracket
1511 Position adjustment unit
1521, 1522 Height adjustment unit
2011 Measurement room
2021 Floor surface
2031, 2032 Side wall surface
2033 Back wall surface
2111, 2112 Shield
3121, 3122 Support portion
3211, 3212, 4211, 4212 Reference sensor holding portion
3311, 3312, 4311, 4312 Hole
3411, 3412, 4411, 4412 Reference sensor
4111, 4112 Reference sensor support portion
A1, A11, B1, B11 Right leg portion
A2, A12, B2, B12 Left leg portion
A3, A13, B3, B13, B23 Platform portion
P1 Distance
P11, P12 Direction
Q1, Q2, Q11, Q12, Q111 Member

What is claimed is:

1. A measuring device comprising:
a first fixing body;
one or more sensors; and
a sensor fixing body configured to fix the one or more sensors for detecting a biological signal,
wherein the first fixing body and the sensor fixing body have separate structures,
the first fixing body is provided with a plate disposed at a position corresponding to the one or more sensors, and
the plate includes a frame and a member provided on a surface of the frame.

2. The measuring device according to claim 1, further comprising:
a sensor holding portion configured to hold the one or more sensors in the sensor fixing body,
wherein the sensor holding portion has a mechanism that holds the one or more sensors.

3. The measuring device according to claim 2,
wherein the sensor holding portion protrudes from an end portion of the sensor fixing body to a side of the plate, and
the sensor holding portion is not in contact with the plate.

4. The measuring device according to claim 2,
wherein the sensor fixing body is provided with a height adjustment unit that adjusts a height of the sensor holding portion and a position adjustment unit that adjusts a position in a direction of the sensor holding portion other than the height.

5. The measuring device according to claim 1, further comprising:
a stand provided on the first fixing body.

6. The measuring device according to claim 1, wherein the sensor fixing body is provided with a cable holding portion that holds a cable of the one or more sensors.

7. The measuring device according to claim 1, wherein one or both of the first fixing body and the sensor fixing body are provided with a fixture for positioning.

8. The measuring device according to claim 7, further comprising:
a measurement room,
wherein one or both of the first fixing body and the sensor fixing body is fixed to one or both of a wall surface and a floor surface of the measurement room by the fixture for positioning.

9. The measuring device according to claim 1, wherein the one or more sensors comprise a plurality of magnetic sensors.

10. The measuring device according to claim 1, wherein the first fixing body is a subject fixing body configured to hold a posture of a subject, and
the one or more sensors comprise a plurality of sensors, each of which detects the biological signal of the subject.

11. The measuring device according to claim 1, further comprising:
a reference sensor configured to detect a reference signal to curb noise that is superimposed on the biological signal detected by the one or more sensors; and
a reference sensor holding portion configured to hold the reference sensor.

* * * * *